United States Patent
Sato

(10) Patent No.: US 11,583,241 B2
(45) Date of Patent: Feb. 21, 2023

(54) ULTRASOUND DIAGNOSIS APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventor: Takeshi Sato, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 1098 days.

(21) Appl. No.: 16/203,082

(22) Filed: Nov. 28, 2018

(65) Prior Publication Data

US 2019/0159750 A1    May 30, 2019

(30) Foreign Application Priority Data

Nov. 30, 2017  (JP) .............................. JP2017-230840

(51) Int. Cl.
   *A61B 6/00*    (2006.01)
   *A61B 8/06*    (2006.01)
   (Continued)

(52) U.S. Cl.
   CPC .............. *A61B 8/06* (2013.01); *A61B 8/488* (2013.01); *A61B 8/5207* (2013.01);
   (Continued)

(58) Field of Classification Search
   CPC combination set(s) only.
   See application file for complete search history.

(56) References Cited

U.S. PATENT DOCUMENTS

2015/0282787 A1* 10/2015 Sato ..................... A61B 8/5246
                                                             600/441
2015/0320395 A1* 11/2015 Sato ....................... A61B 8/06
                                                             600/455
(Continued)

FOREIGN PATENT DOCUMENTS

| JP | 2014-158698 | 9/2014 |
| JP | 2017-55845  | 3/2017 |
| JP | 2017-55846  | 3/2017 |

OTHER PUBLICATIONS

U.S. Appl. No. 14/803,726, filed Jul. 20, 2015, 2015/0320395 A1, Takeshi Sato.

(Continued)

*Primary Examiner* — Joel F Brutus
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured: to generate a piece of reflected-wave data by performing a phased addition process while using reflected-wave signals generated by transmitting an ultrasound wave with respect to mutually the same scanning line; to speculate a degree of saturation of the reflected-wave signals observed before the phased addition process on the basis of a relationship between signals and noise in a data sequence represented by a set made up of pieces of the reflected-wave data; and to output a result of the speculation. The processing circuitry is configured to cause a display to display data based on the result of the speculation.

15 Claims, 13 Drawing Sheets

(51) Int. Cl.
*A61B 8/08* (2006.01)
*G01S 7/52* (2006.01)
*G01S 15/89* (2006.01)
*A61B 8/00* (2006.01)

(52) U.S. Cl.
CPC ...... *G01S 7/52077* (2013.01); *G01S 15/8977* (2013.01); *G01S 15/8981* (2013.01); *A61B 8/4254* (2013.01); *A61B 8/463* (2013.01); *A61B 8/5246* (2013.01); *A61B 8/5269* (2013.01); *A61B 8/54* (2013.01); *G01S 15/8915* (2013.01)

(56) References Cited

U.S. PATENT DOCUMENTS

2017/0071569 A1  3/2017  Sato
2017/0071575 A1  3/2017  Sato

OTHER PUBLICATIONS

U.S. Appl. No. 15/257,459, filed Sep. 6, 2016, 2017/0071569 A1, Takeshi Sato.
U.S. Appl. No. 15/254,303, filed Sep. 1, 2016, 2017/0071575 A1, Takeshi Sato.

* cited by examiner

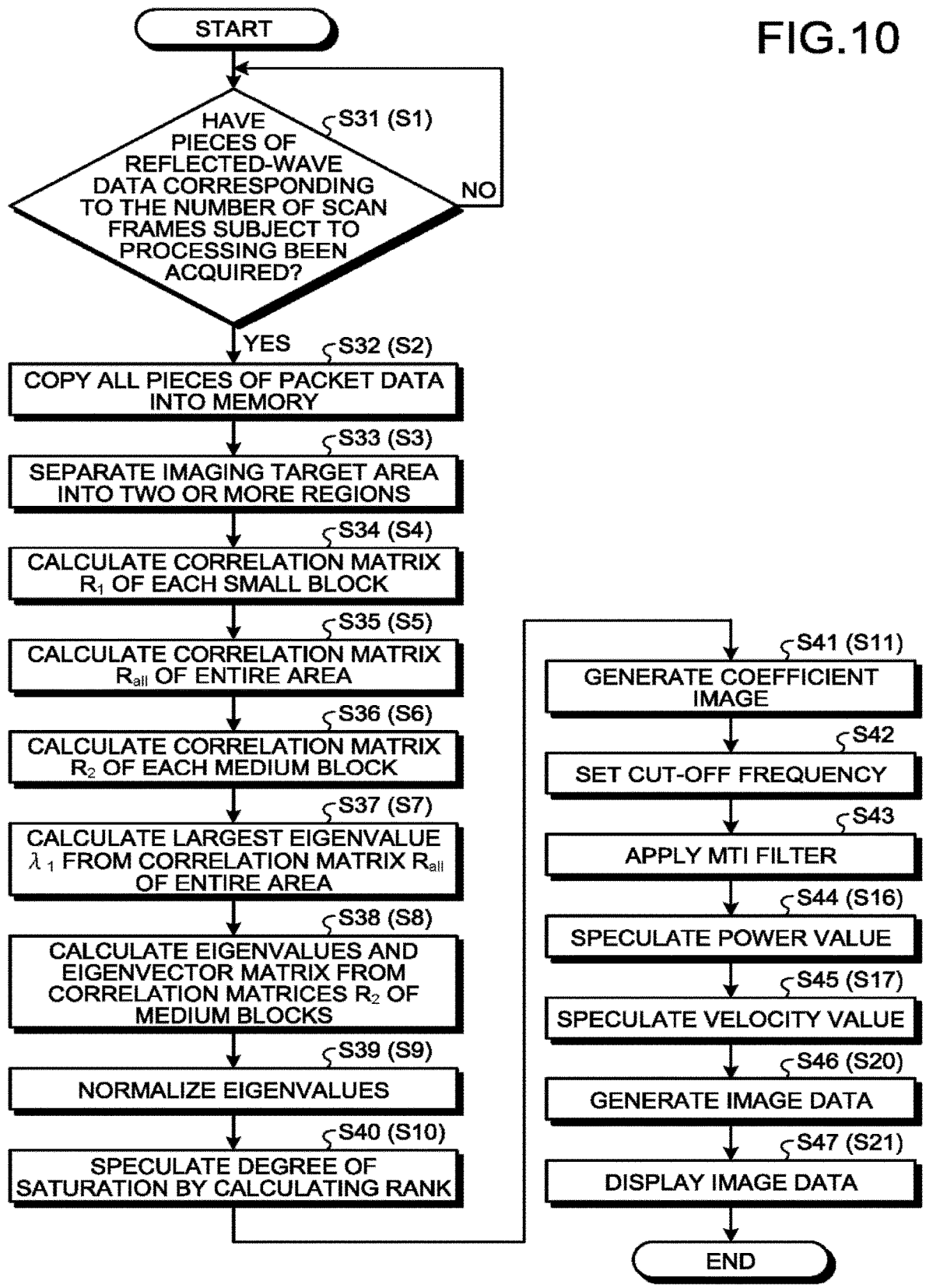

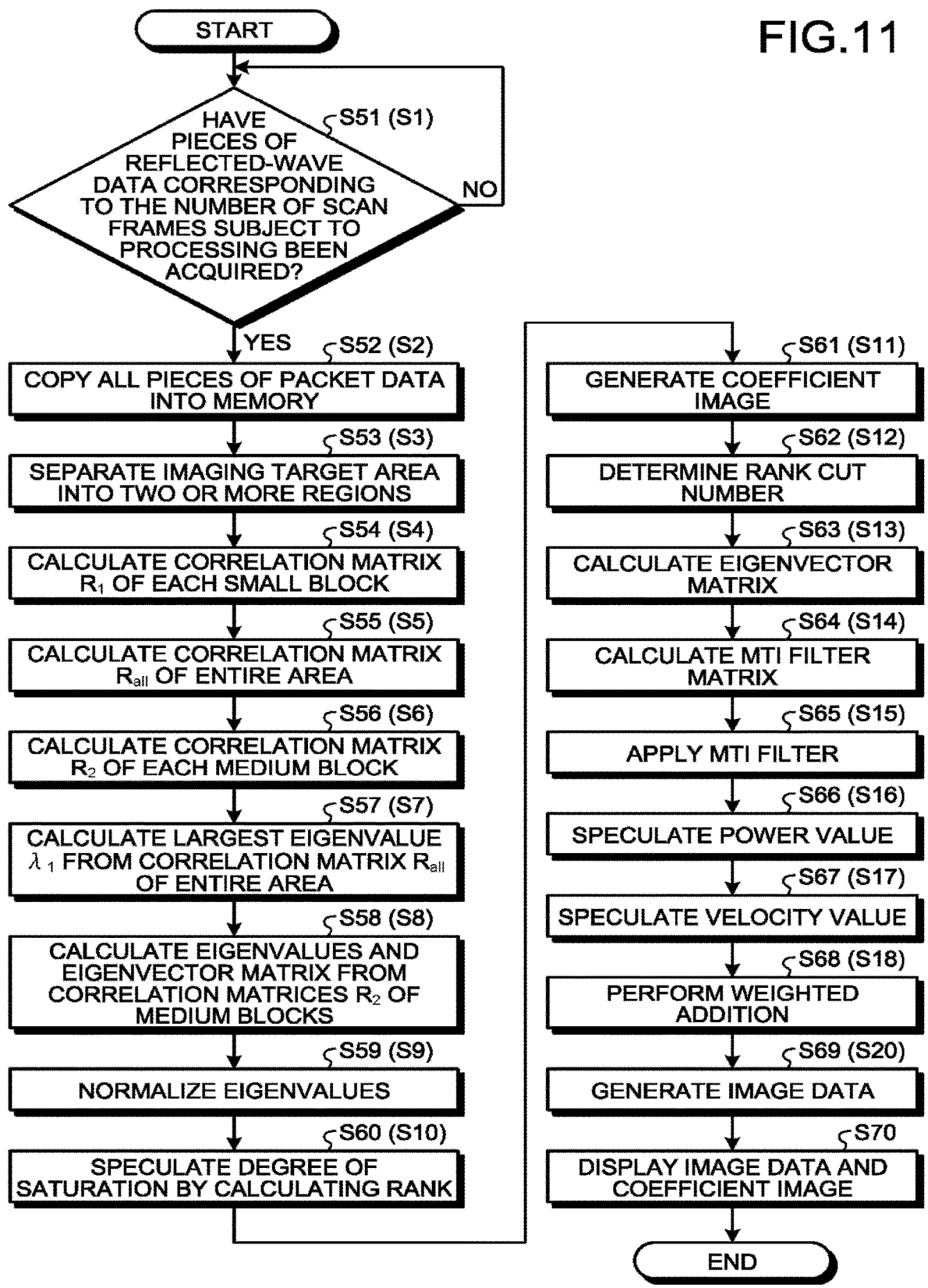

ULTRASOUND DIAGNOSIS APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2017-230840, filed on Nov. 30, 2017; the entire contents of which are incorporated herein by reference.

FIELD

Embodiments described herein relate generally to an ultrasound diagnosis apparatus, a medical image processing apparatus, and a medical image processing method.

BACKGROUND

In recent years, for use in Color Flow Mapping (CFM) methods, a technique has been developed with which it is possible to display a small blood flow having low flowing velocity lower than the velocity of movements of the imaged patient, although such a display had conventionally been impossible as being hindered by tissues of the patient. For example, a blood flow imaging method employing an adaptive Moving Target Indicator (MTI) filter that uses an eigenvector has been disclosed. To implement this blood flow imaging method, a method has been disclosed by which a correlation matrix is calculated for an entire image so as to apply a single MTI filter matrix to the entire image, and another method has also been disclosed by which an image is separated into sections to calculate correlation matrices and to apply mutually-different MTI filter matrices to blocks.

When such a blood flow imaging method employing the adaptive MTI filter is implemented, a significant side lobe may be exhibited when signals are saturated. In particular, when a plane wave transmission or a diffuse wave transmission is performed, a problem arises where an arc-shaped artifact may occur. To cope with this problem, a method has been disclosed by which, for example, saturation is detected with respect to signals observed before a beam forming process.

BRIEF DESCRIPTION OF THE DRAWINGS

FIG. 10 is a flowchart illustrating a processing procedure performed by an ultrasound diagnosis apparatus according to a second embodiment; and FIG. 11 is a flowchart illustrating a processing procedure performed by an ultrasound diagnosis apparatus according to a third embodiment.

DETAILED DESCRIPTION

An ultrasound diagnosis apparatus according to an embodiment includes processing circuitry. The processing circuitry is configured: to generate a piece of reflected-wave data by performing a phased addition process while using reflected-wave signals generated by transmitting an ultrasound wave with respect to mutually the same scanning line; to speculate a degree of saturation of the reflected-wave signals observed before the phased addition process on the basis of a relationship between signals and noise in a data sequence represented by a set made up of pieces of the reflected-wave data; and to output a result of the speculation. The processing circuitry is configured to cause a display to display data based on the result of the speculation.

Exemplary embodiments of an ultrasound diagnosis apparatus, a medical image processing apparatus, and a medical image processing method will be explained below, with reference to the accompanying drawings. Possible embodiments are not limited to the embodiments described below. Further, the description of each of the embodiments is, in principle, similarly applicable to any other embodiment.

First Embodiment

First, a configuration of an ultrasound diagnosis apparatus according to a first embodiment will be explained.

Figure 1:
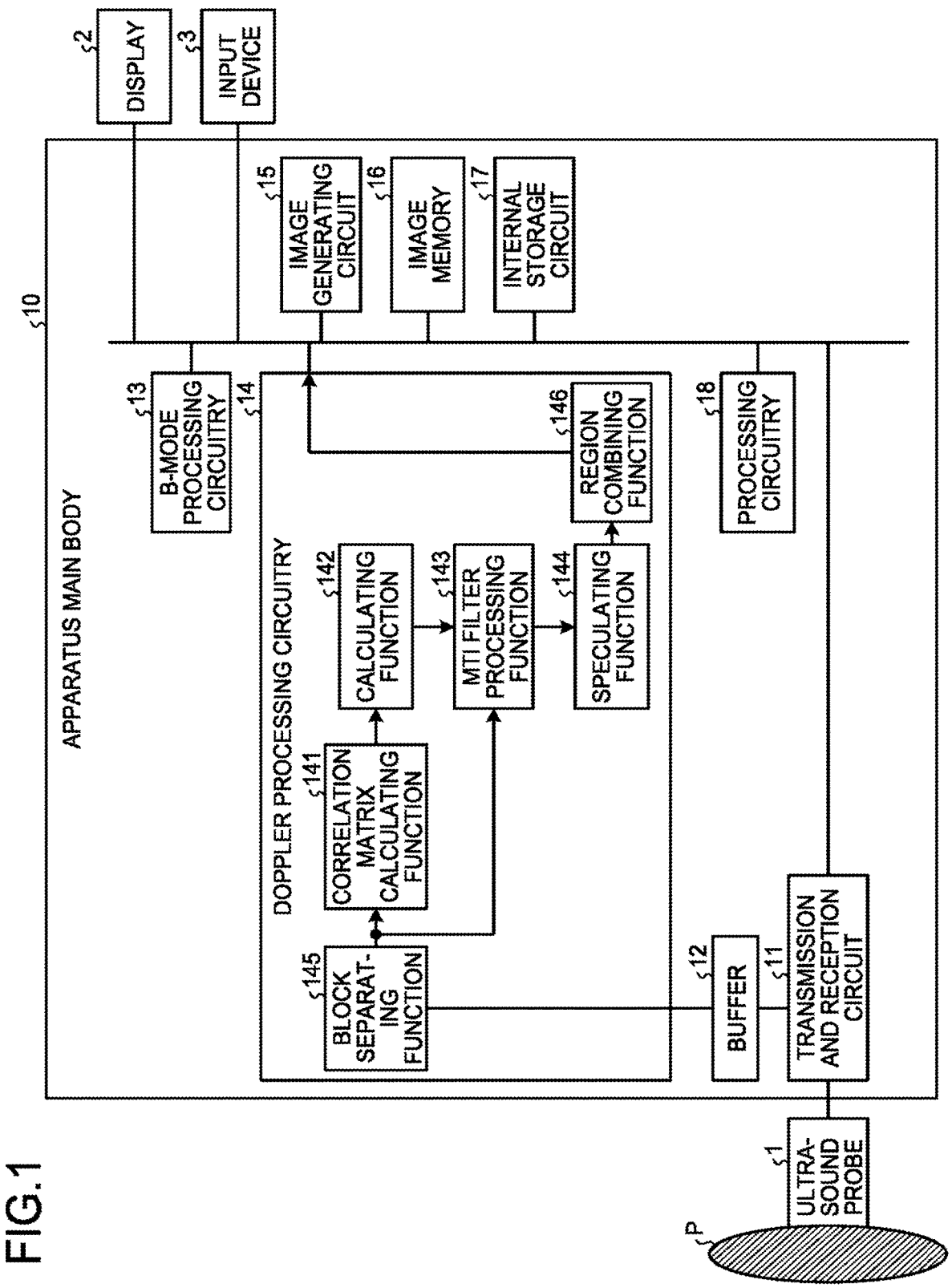
FIG. 1 is a block diagram illustrating an exemplary configuration of an ultrasound diagnosis apparatus according to a first embodiment.

FIG. 1 is a block diagram illustrating an exemplary configuration of the ultrasound diagnosis apparatus according to the first embodiment. As illustrated in FIG. 1, the ultrasound diagnosis apparatus according to the first embodiment includes an ultrasound probe 1, a display 2, an input device 3, and an apparatus main body 10.

To transmit and receive ultrasound waves, the ultrasound probe 1 is connected to the apparatus main body 10. For example, the ultrasound probe 1 includes a plurality of piezoelectric transducer elements. Each of the plurality of piezoelectric transducer elements is configured to generate an ultrasound wave on the basis of a drive signal supplied thereto from a transmission and reception circuit 11 (explained later) included in the apparatus main body 10. Further, each of the plurality of piezoelectric transducer elements included in the ultrasound probe 1 is configured to receive a reflected wave from an examined subject (hereinafter, "patient") P and to convert the received reflected wave into an electrical signal. Further, the ultrasound probe 1 includes matching layers provided for the piezoelectric transducer elements, as well as a backing member or the like that prevents the ultrasound waves from propagating rearward from the piezoelectric transducer elements. In this situation, the ultrasound probe 1 is detachably connected to the apparatus main body 10.

When an ultrasound wave is transmitted from the ultrasound probe 1 to the patient P, the transmitted ultrasound wave is repeatedly reflected on a surface of discontinuity of acoustic impedances at a tissue in the body of the patient P and is received as a reflected-wave signal by each of the plurality of piezoelectric transducer elements included in the ultrasound probe 1. The amplitude of the received reflected-wave signal is dependent on the difference between the acoustic impedances on the surface of discontinuity on which the ultrasound wave is reflected.

When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The first embodiment is applicable to both when the ultrasound probe 1 is a one-dimensional (1D) array probe configured to scan the patient P two-dimensionally and when the ultrasound probe 1 is a mechanical four-dimensional (4D) probe or a two-dimensional (2D) array probe configured to scan the patient P three-dimensionally.

The input device 3 includes a mouse, a keyboard, a button, a panel switch, a touch command screen, a foot switch, a trackball, a joystick, and/or the like. The input device 3 is configured to receive various types of setting requests from an operator of the ultrasound diagnosis apparatus and to transfer the received various types of setting requests to the apparatus main body 10.

The display 2 is configured to display a Graphical User Interface (GUI) used by the operator of the ultrasound diagnosis apparatus to input the various types of setting requests through the input device 3 and to display ultrasound image data or the like generated by the apparatus main body 10.

The apparatus main body 10 is an apparatus configured to generate the ultrasound image data on the basis of the reflected-wave signals received by the ultrasound probe 1.

The apparatus main body 10 illustrated in FIG. 1 is an apparatus capable of generating two-dimensional ultrasound image data on the basis of two-dimensional reflected-wave signals and also capable of generating three-dimensional ultrasound image data on the basis of three-dimensional reflected-wave signals. It should be noted, however, that the first embodiment is also applicable when the apparatus main body 10 is an apparatus exclusively for two-dimensional data.

As illustrated in FIG. 1, the apparatus main body 10 includes the transmission and reception circuit 11, a buffer 12, B-mode processing circuitry 13, Doppler processing circuitry 14, an image generating circuit 15, an image memory 16, an internal storage circuit 17, and processing circuitry 18.

On the basis of an instruction from the processing circuitry 18 (explained later), the transmission and reception circuit 11 is configured to control transmission and reception of ultrasound waves performed by the ultrasound probe 1. The transmission and reception circuit 11 includes a pulse generator, a transmission delay circuit, a pulser, and the like and is configured to supply the drive signal to the ultrasound probe 1. The pulse generator is configured to repeatedly generate a rate pulse used for forming a transmission ultrasound wave, at a predetermined Pulse Repetition Frequency (PRF). Further, the transmission delay circuit is configured to apply a delay period that is required to converge the ultrasound wave generated from the ultrasound probe 1 into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 1 with timing based on the rate pulses. In other words, by varying the delay periods applied to the rate pulses, the transmission delay circuit is able to arbitrarily adjust the transmission directions of the ultrasound waves transmitted from the surfaces of the piezoelectric transducer elements.

In this situation, the transmission and reception circuit 11 has a function that is able to instantly change the transmission frequency, the transmission drive voltage, and the like, for the purpose of executing a predetermined scan sequence on the basis of an instruction from the processing circuitry 18 (explained later). In particular, the function to change the transmission drive voltage is realized by using a linear-amplifier-type transmission circuit of which the value can be instantly switched or by using a mechanism configured to electrically switch between a plurality of power source units.

For example, under the control of the processing circuitry 18, the transmission and reception circuit 11 is configured to cause the ultrasound probe 1 to perform an ultrasound scan that uses an intra-frame data sequence as a Doppler data sequence (see Japanese Patent No. 3,724,846 and Japanese Patent Application Laid-open No. 2014-42823). For example, under the control of the processing circuitry 18, the transmission and reception circuit 11 causes the ultrasound probe 1 to perform a first ultrasound scan by which information about movements of moving members in a first scan range is obtained and further causes the ultrasound probe 1 to perform, in a time-division manner during the first ultrasound scan, an ultrasound scan in each of a plurality of sectional ranges into which a second scan range is separated, as a second ultrasound scan by which information about shapes of tissues in the second scan range is obtained.

Further, the transmission and reception circuit 11 includes an amplifying circuit, an Analog/Digital (A/D) converter, a reception delay circuit, an adder, a quadrature detecting circuit, and the like and is configured to generate reflected-wave data by performing various types of processes on the reflected-wave signals received by the ultrasound probe 1. The amplifying circuit is configured to amplify the reflected-wave signal for each of the channels and to perform a gain correcting process. The A/D converter is configured to perform an A/D conversion on the gain-corrected reflected-wave signals. The reception delay circuit is configured to apply a reception delay period required to determine reception directionality, to the digital data. The adder is configured to perform an adding process on the reflected-wave signals to which the reception delay period has been applied by the reception delay circuit. As a result of the adding process performed by the adder, reflected components from the direction corresponding to the reception directionality of the reflected-wave signals are emphasized. In this situation, the process of performing the adding process after adjusting phases by delaying the reception for each of the reflected-wave signals corresponding to the elements may be referred to as a phased addition process or a beam forming process.

Further, the quadrature detecting circuit is configured to convert the output signal from the adder into an In-phase signal (an I signal) and a Quadrature-phase signal (a Q signal) that are in a baseband. Further, the quadrature detecting circuit is configured to store the I signal and the Q signal (hereinafter, "IQ signals") into the buffer 12 as the reflected-wave data. Alternatively, the quadrature detecting circuit may store the output signal from the adder into the buffer 12 after converting the output signal into an analytic signal. The IQ signals or the analytic signal serves as a signal (a reception signal) containing phase information. In the following sections, the reflected-wave data output by the transmission and reception circuit 11 may be referred to as a reception signal.

When the patient P is to be two-dimensionally scanned, the transmission and reception circuit 11 is configured to cause a two-dimensional ultrasound beam to be transmitted from the ultrasound probe 1. Further, the transmission and reception circuit 11 is configured to generate two-dimensional reflected-wave data from the two-dimensional reflected-wave signals received by the ultrasound probe 1. In contrast, when the patient P is to be three-dimensionally scanned, the transmission and reception circuit 11 is configured to cause a three-dimensional ultrasound beam to be transmitted from the ultrasound probe 1. Further, the transmission and reception circuit 11 is configured to generate three-dimensional reflected-wave data from the three-dimensional reflected-wave signals received by the ultrasound probe 1.

The buffer 12 is a buffer configured to temporarily store therein the reflected-wave data (the I/Q signals) generated by the transmission and reception circuit 11. More specifically, the buffer 12 is configured to store therein the I/Q signals corresponding to a number of frames or the I/Q signals corresponding to a number of volumes. For example, the buffer 12 may be a First-In/First-Out (FIFO) memory and configured to store therein the I/Q signals corresponding to a predetermined number of frames. Further, for example, when the I/Q signals corresponding to another frame is newly generated by the transmission and reception circuit 11, the buffer 12 is configured to discard the I/Q signals corresponding to the one frame that was generated earliest and to store therein the newly-generated I/Q signals corresponding to the one frame.

The B-mode processing circuitry 13 and the Doppler processing circuitry 14 are each a signal processing unit configured to perform various types of signal processing processes on the reflected-wave data generated from the reflected-wave signals by the transmission and reception circuit 11. The B-mode processing circuitry 13 is configured to generate data (B-mode data) in which the signal intensity corresponding to each of a plurality of sampling points is expressed by a degree of brightness, by performing a logarithmic amplification, an envelope detecting process, a logarithmic compression, and/or the like on the reflected-wave data (the I/Q signals) read from the buffer 12.

Also, by performing a filtering process, the B-mode processing circuitry 13 is capable of varying the frequency band to be rendered in images, by varying the detected frequency. By using this function of the B-mode processing circuitry 13, the ultrasound diagnosis apparatus according to the first embodiment is capable of executing a harmonic imaging process such as a Contrast Harmonic Imaging (CHI) process, a Tissue Harmonic Imaging (THI) process, or the like. In other words, from the reflected-wave data of the patient P into whom a contrast agent has been injected, the B-mode processing circuitry 13 is configured to separate reflected-wave data (harmonic data or subharmonic data) of a harmonic component reflected by a contrast agent (microbubbles or bubbles) and reflected-wave data (fundamental wave data) of a fundamental wave component reflected by tissues on the inside of the patient P. The B-mode processing circuitry 13 is capable of generating B-mode data used for generating contrast enhanced image data, from reflected-wave data (a reception signal) of the harmonic component.

Further, by using the filtering function of the B-mode processing circuitry 13 mentioned above, the ultrasound diagnosis apparatus according to the first embodiment is capable of executing the Tissue Harmonic Imaging (THI) process. In other words, from the reflected-wave data of the patient P, the B-mode processing circuitry 13 is capable of separating the harmonic data or the subharmonic data represented by reflected-wave data (a reception signal) of the harmonic component. Further, the B-mode processing circuitry 13 is capable of generating B-mode data used for generating tissue image data from which noise components are eliminated, from the reflected-wave data (the reception signal) of the harmonic component.

Further, when performing the harmonic imaging process such as CHI or THI, the B-mode processing circuitry 13 is capable of extracting the harmonic component by using a method different from the abovementioned method that employs the filtering process. During the harmonic imaging process, an imaging method may be implemented such as an Amplitude Modulation (AM) method; a Phase Modulation (PM) method; or an AMPM method in which the AM method and the PM method are combined together. According to the AM method, the PM method, and the AMPM method, ultrasound wave transmission sessions having mutually-different amplitude levels and/or mutually-different phases are performed multiple times on mutually the same scanning line. As a result, the transmission and reception circuit 11 generates and outputs a plurality of pieces of reflected-wave data (the reception signals) for each of the scanning lines. Further, the B-mode processing circuitry 13 extracts the harmonic component by performing an adding/subtracting process corresponding to a modulation method on the plurality of pieces of reflected-wave data (the reception signals) corresponding to the scanning lines. After that, the B-mode processing circuitry 13 generates B-mode data by performing the envelope detecting process or the like on the reflected-wave data (the reception signals) of the harmonic component.

For example, when the PM method is implemented, according to a scan sequence set by the processing circuitry 18, the transmission and reception circuit 11 causes ultrasound waves having opposite phase polarities and mutually the same amplitude levels (e.g., −1 and 1) to be transmitted twice for each of the scanning lines. Further, the transmission and reception circuit 11 generates a reception signal resulting from the transmission corresponding to "−1" and another reception signal resulting from the transmission corresponding to "1", so that the B-mode processing circuitry 13 adds the two reception signals together. As a result, a signal is generated from which the fundamental wave component has been eliminated and in which a second harmonic component primarily remains. Further, the B-mode processing circuitry 13 generates THI B-mode data and/or CHI B-mode data by performing an envelope detecting process or the like on the generated signal.

Alternatively, for example, for THI processes, a method has been put into practical use by which images are rendered while using the second harmonic component included in the reception signal and a combination tone component. According to an image rendering method that uses the combination tone component, for example, the ultrasound probe 1 is caused to transmit a transmission ultrasound wave having a combined waveform obtained by combining together a first fundamental wave of which the center frequency is equal to "f1" and a second fundamental wave of which the center frequency is equal to "f2" that is higher than "f1". The combined waveform is a waveform obtained by combining together the waveform of the first fundamental wave and the waveform of the second fundamental wave, while the phases of the two waveforms are adjusted so as to generate the combination tone component having the same polarity as that of the second harmonic component. The transmission and reception circuit 11 causes the transmission ultrasound wave having the combined waveform to be transmitted twice, for example, while inverting the phase thereof. In that situation, for example, by adding the two reception signals together, the B-mode processing circuitry 13 extracts a harmonic component from which the fundamental wave component has been eliminated and in which the combination tone component and the second harmonic component primarily remain, and subsequently performs the envelope detecting process or the like.

By performing a frequency analysis on the reflected-wave data read from the buffer 12, the Doppler processing circuitry 14 is configured to generate data (Doppler data) obtained by extracting movement information based on a Doppler effect about moving members that are present in a scan range. More specifically, as the movement information of the moving members, the Doppler processing circuitry 14 generates Doppler data with respect to each of multiple sampling points, on the basis of an average velocity value, an average dispersion value, an average power value, and/or the like. In this situation, the moving members may be, for example, a blood flow, a tissue such as the cardiac wall, and a contrast agent. The movement information of the moving members may also be referred to as moving member information. As the movement information of a blood flow (blood flow information), the Doppler processing circuitry 14 according to the present embodiment generates the Doppler data obtained by speculating an average velocity value of the blood flow, a dispersion value of blood flow velocity values, a power value of a blood flow signal, and/or the like, with respect to each of the multiple sampling points.

By using the abovementioned function of the Doppler processing circuitry 14, the ultrasound diagnosis apparatus according to the present embodiment is capable of implementing a color Doppler method that may also be called a Color Flow Mapping (CFM) method. According to the CFM method, the transmission and reception of an ultrasound wave is performed multiple times on a plurality of scanning lines. Further, according to the CFM method, by applying a Moving Target Indicator (MTI) filter to a data sequence of mutually the same position, a signal derived from a blood flow is extracted, while suppressing a signal (a clutter signal) derived from stationary or slowly-moving tissues. Further, according to the CFM method, on the basis of the blood flow signal, the blood flow information such as a velocity value of the blood flow, a dispersion value of the blood flow, a power value of the blood flow, and/or the like are speculated.

The image generating circuit 15 (explained later) is configured to generate ultrasound image data (color Doppler image data) two-dimensionally displaying a distribution of results of the speculation in color, for example. Further, the display 2 is configured to display the color Doppler image data.

Generally speaking, as MTI filters, filters having a fixed coefficient such as Butterworth Infinite Impulse Response (IIR) filters and polynomial regression filters are usually used. In contrast, as the MTI filter, the Doppler processing circuitry 14 according to the present embodiment is configured to use an adaptive MTI filter of which the coefficient is varied in accordance with an input signal. More specifically, as the adaptive MTI filter, the Doppler processing circuitry 14 according to the present embodiment is configured to use a filter called "eigenvector regression filter". In the following sections, the "eigenvector regression filter" realized with an adaptive MTI filter using eigenvectors will be referred to as an "eigenvector MTI filter".

The eigenvector MTI filter is configured to calculate eigenvectors on the basis of a correlation matrix and to further calculate a coefficient to be used in the clutter component suppressing process on the basis of the calculated eigenvectors. This method is an application of methods used in principal component analyses, Karhunen-Loeve transform schemes, and eigenspace schemes.

As illustrated in FIG. 1, the Doppler processing circuitry 14 according to the first embodiment that employs the eigenvector MTI filter is configured to execute: a correlation matrix calculating function 141, a calculating function 142, an MTI filter processing function 143, a speculating function 144, a block separating function 145, and a region combining function 146. In this situation, for example, the processing functions executed by the constituent elements of the Doppler processing circuitry 14 illustrated in FIG. 1, namely, the correlation matrix calculating function 141, the calculating function 142, the MTI filter processing function 143, the speculating function 144, the block separating function 145, and the region combining function 146 are each recorded in the internal storage circuit 17 in the form of a computer-executable program. For example, the Doppler processing circuitry 14 is a processor and is configured to read the programs from the internal storage circuit 17 and to realize the functions corresponding to the read programs by executing the read programs. In other words, the Doppler processing circuitry 14 that has read the programs has the functions illustrated within the Doppler processing circuitry 14 in FIG. 1.

The correlation matrix calculating function 141 is configured to calculate a correlation matrix of the scan range from a data sequence of sequential pieces of reflected-wave data in mutually the same position (mutually the same sampling point). For example, the calculating function 142 is configured to calculate eigenvalues of the correlation matrix and eigenvectors corresponding to the calculated eigenvalues.

For example, the calculating function 142 calculates, as a filter matrix used for suppressing the clutter component, a matrix obtained by reducing the rank of the matrix in which the eigenvectors are arranged on the basis of the magnitudes of the eigenvalues.

By using the filter matrix, the MTI filter processing function 143 is configured to output a data sequence obtained by extracting a blood flow signal derived from the blood flow while suppressing the clutter component, from the data sequence of the sequential pieces of reflected-wave data in mutually the same position (mutually the same sampling point).

The speculating function 144 is configured to speculate blood flow information by performing a calculation such as an autocorrelation calculation while using the data output by the MTI filter processing function 143 and to further output the speculated blood flow information as Doppler data.

The block separating function 145 is configured to separate the scan range formed with the plurality of scanning lines into two or more regions. The region combining function 146 is configured to combine together pieces of data of the separated regions. Specific processes performed by the Doppler processing circuitry 14 according to the first embodiment will be explained in detail later. Further, the calculating function 142 according to the first embodiment is an example of a saturation speculating unit. The MTI filter processing function 143, the speculating function 144, and the region combining function 146 are examples of an extracting unit.

The B-mode processing circuitry 13 and the Doppler processing circuitry 14 illustrated in FIG. 1 are capable of processing both two-dimensional reflected-wave data and three-dimensional reflected-wave data. In other words, the B-mode processing circuitry 13 is configured to generate two-dimensional B-mode data from the two-dimensional reflected-wave data and to generate three-dimensional B-mode data from the three-dimensional reflected-wave data. Further, the Doppler processing circuitry 14 is configured to generate two-dimensional Doppler data from the two-dimensional reflected-wave data and to generate three-dimensional Doppler data from the three-dimensional reflected-wave data.

The image generating circuit 15 is configured to generate the ultrasound image data from the data generated by the B-mode processing circuitry 13 and the Doppler processing circuitry 14. The image generating circuit 15 is configured to generate two-dimensional B-mode image data in which the intensities of reflected waves are expressed with degrees of brightness, from the two-dimensional B-mode data generated by the B-mode processing circuitry 13. Further, the image generating circuit 15 is configured to generate two-dimensional Doppler image data in which the blood flow information is rendered in an image from the two-dimensional Doppler data generated by the Doppler processing circuitry 14. In other words, the image generating circuit 15 is configured to generate the image data based on the moving member information. The two-dimensional Doppler image data may be velocity image data, dispersion image data, power image data or image data combining any of these. As the Doppler image data, the image generating circuit 15 is configured to generate color Doppler image data in which the blood flow information is displayed in color and to generate Doppler image data in which a certain piece of blood flow information is displayed on a gray scale.

In this situation, generally speaking, the image generating circuit 15 converts (by performing a scan convert process) a scanning line signal sequence from an ultrasound scan into a scanning line signal sequence in a video format used by, for example, television and generates display-purpose ultrasound image data. More specifically, the image generating circuit 15 generates the display-purpose ultrasound image data by performing a coordinate transformation process compliant with the ultrasound scanning mode used by the ultrasound probe 1. Further, as various types of image processing processes besides the scan convert process, the image generating circuit 15 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuit 15 combines text information of various parameters, scale graduations, body marks, and the like with the ultrasound image data.

In other words, the B-mode data and the Doppler data are each ultrasound image data before the scan convert process. The data generated by the image generating circuit 15 is the display-purpose ultrasound image data after the scan convert process. The B-mode data and the Doppler data may each also be referred to as "raw data". The image generating circuit 15 generates the display-purpose two-dimensional ultrasound image data from the two-dimensional ultrasound image data before the scan convert process.

Further, the image generating circuit 15 is configured to generate three-dimensional B-mode image data by performing a coordinate transformation process on the three-dimensional B-mode data generated by the B-mode processing circuitry 13. Further, the image generating circuit 15 is configured to generate three-dimensional Doppler image data by performing a coordinate transformation process on the three-dimensional Doppler data generated by the Doppler processing circuitry 14. The image generating circuit 15 is configured to generate the "three-dimensional B-mode image data and three-dimensional Doppler image data" each as "three-dimensional ultrasound image data (volume data)".

Further, for the purpose of generating various types of two-dimensional image data used for causing the display 2 to display the volume data, the image generating circuit 15 is configured to perform a rendering process on the volume data.

Examples of the rendering process performed by the image generating circuit 15 includes a process of generating Multi Planar Reconstruction (MPR) image data from the volume data by implementing an MPR method. Further, another example of the rendering process performed by the image generating circuit 15 is a Volume Rendering (VR) process by which two-dimensional image data reflecting three-dimensional information is generated. The image generating circuit 15 is an example of an image generating unit.

The image memory 16 is a memory configured to store therein the display-purpose image data generated by the image generating circuit 15. Further, the image memory 16 is also capable of storing therein any of the data generated by the B-mode processing circuitry 13 and the Doppler processing circuitry 14. After a diagnosis process, for example, the operator is able to invoke any of the B-mode data and the Doppler data stored in the image memory 16. The invoked B-mode data and Doppler data can serve as display-purpose ultrasound image data after being routed through the image generating circuit 15. Further, the image memory 16 is also capable of storing therein the reflected-wave data output by the transmission and reception circuit 11.

The internal storage circuit 17 is configured to store therein control programs for performing ultrasound transmissions and receptions, image processing processes, and display processes as well as various types of data such as diagnosis information (e.g., patient's IDs, medical doctors' observations), diagnosis protocols, various types of body marks, and the like. Further, the internal storage circuit 17 may be used, as necessary, for saving therein any of the image data stored in the image memory 16, and the like. Further, the data stored in the internal storage circuit 17 may be transferred to an external apparatus via an interface (not illustrated). Further, the internal storage circuit 17 is also capable of storing therein data transferred thereto from an external apparatus via an interface (not illustrated).

The processing circuitry 18 is configured to control the overall processes performed by the ultrasound diagnosis apparatus. More specifically, the processing circuitry 18 is configured to control processes performed by the transmission and reception circuit 11, the B-mode processing circuitry 13, the Doppler processing circuitry 14, and the image generating circuit 15, on the basis of the various types of setting requests input by the operator via the input device 3 and the various types of control programs and the various types of data read from the internal storage circuit 17. For example, the processing circuitry 18 is configured to control an ultrasound scan, by controlling the ultrasound probe 1 via the transmission and reception circuit 11. Normally, according to the CFM method, together with color Doppler image data represented by blood flow image data, B-mode image data represented by tissue image data is displayed. To realize the display in this manner, the processing circuitry 18 causes the ultrasound probe 1 to perform the first ultrasound scan to obtain the blood flow information in the first scan range. For example, the first ultrasound scan is an ultrasound scan performed for acquiring color Doppler image data in a Doppler mode. Further, together with the first ultrasound scan, the processing circuitry 18 causes the ultrasound probe 1 to perform the second ultrasound scan to obtain information about the shapes of the tissues in the second scan range. For example, the second ultrasound scan is an ultrasound scan performed for acquiring B-mode image data in a B-mode.

The processing circuitry 18 causes the first ultrasound scan and the second ultrasound scan to be performed, by controlling the ultrasound probe 1 via the transmission and reception circuit 11. As for the first scan range and the second scan range, the two scan ranges may be the same as each other. Alternatively, the first scan range may be smaller than the second scan range. Conversely, the second scan range may be smaller than the first scan range.

Further, the processing circuitry 18 is configured to exercise control so that the display 2 displays any of the display-purpose ultrasound image data stored in the image memory 16 and the internal storage circuit 17. The transmission and reception circuit 11 and the like built in the apparatus main body 10 may be configured by using hardware such as an integrated circuit or may be configured as a modularized program by using software. The processing circuitry 18 is an example of a controlling unit.

An overall configuration of the ultrasound diagnosis apparatus according to the first embodiment has thus been explained. The ultrasound diagnosis apparatus according to the first embodiment structured as described above is configured to implement the CFM method by using the blood flow information (the Doppler data) speculated by using the eigenvector MTI filter. As explained above, the Doppler processing circuitry 14 employing the eigenvector MTI filter is configured to calculate the eigenvectors from the correlation matrix.

Incidentally, when the CFM method employing the eigenvector MTI filter is implemented by transmitting a plane wave or a diffuse wave, there is a problem where, when signals become saturated, an arc-shaped artifact may occur due to an increase of a side lobe. As a countermeasure for this problem, a method is known by which a saturation detecting process is performed on channel signals (hereinafter, "CH signals") observed before the beam forming process, for example. It is, however, difficult to realize this method. For example, most of the beam formers that are currently used are configured by using hardware. We are therefore not in an environment where beam formers can freely be controlled by using software. Further, when actually realizing a beam former by using hardware, an increase in the circuit scale can be a problem. Further, when the saturation detecting process and the beam forming process are performed by using software, another problem may arise where the load imposed on the software becomes large, and real-timeness thereof may be impeded.

In contrast, as a comparison example, when the CFM method employing the eigenvector MTI filter is implemented while applying a transmission focus, no arc-shaped artifact is observed because the side lobe from the transmission and reception is suppressed. Accordingly, there seems to be no impact from saturated signals.

However, in the presence of a powerful reflecting member, when reflected-wave signals reflected by the powerful reflecting member become saturated, a problem arises where an image is displayed as if there was a blood flow in the location where the powerful reflecting member is present. In this manner, there is a risk that something that is not actually a blood flow may be mistakenly recognized as a blood flow during diagnosis processes, which may cause a serious clinical problem. In other words, a side lobe caused by saturation from a powerful reflecting member is evidently displayed as an arc-shaped artifact and is thus recognizable. In contrast, saturation in a main lobe does not occur as an arc-shaped artifact, and the impact on the entire image is latent and is thus unrecognizable.

The problem described above does not occur when the powerful reflecting member is completely stationary, because it is possible to completely eliminate the reflected-wave signals reflected by the powerful reflecting member, by using an MTI filter. However, the problem described above occurs when the CH signals become saturated while the powerful reflecting member is moving.

For example, when packet signals for color Doppler from mutually the same location points contain both signals saturated with movements and unsaturated signals in a mixed manner, a part of RF signals in the packet is clipped due to the saturation. As a result, a harmonic wave occurs in a low-frequency Doppler signal resulting from movements of the tissue, and a high Doppler frequency thus occurs. In this situation, because the amplitude of the Doppler signal having the harmonic wave derived from the tissue is small and is not a principal component, such a Doppler signal passes through the MTI filter. For this reason, when the powerful reflecting member is moving, it is not possible to suppress the saturation of the CH signals by using an adaptive MTI filter. In particular, this phenomenon causes a serious impact when a blood flow imaging method is implemented by employing an adaptive MTI filter that uses eigenvectors while the observed blood flow velocity is equal to or smaller than the velocity of the movement of the tissue.

To cope with this situation, in the following sections, a medical image processing method will be explained with which, by using signals observed after the beam forming process, it is possible to solve the problem where, when an echo signal occurring from a powerful reflecting member enters the CH signals observed before the beam forming process, an image is displayed as if a blood flow was present.

Figure 2A:
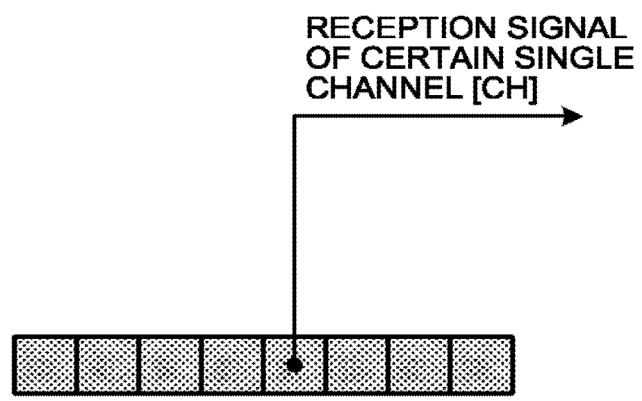
FIG. 2A is a drawing for explaining the first embodiment.
Figure 2B:
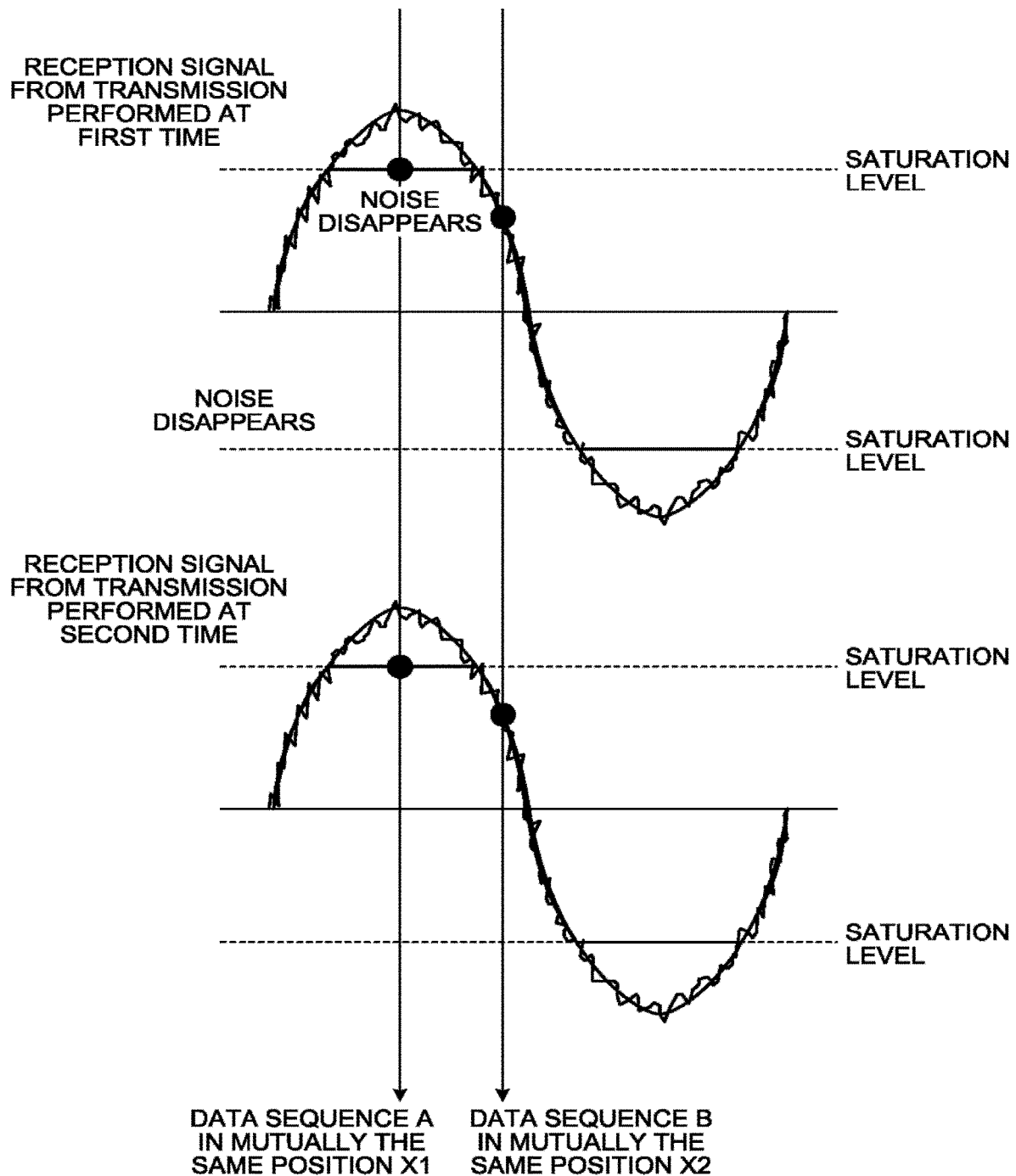
FIG. 2B is another drawing for explaining the first embodiment.

For example, according to the medical image processing method, the ultrasound diagnosis apparatus is configured to speculate the degree of saturation of reflected-wave signals observed before the phased addition process performed by using the reflected-wave signals generated by transmitting an ultrasound wave with respect to mutually the same scanning line, on the basis of a relationship between signals and noise in a data sequence represented by a set made up of pieces of reflected-wave data generated through the phased addition process. FIGS. 2A and 2B are drawings for explaining the first embodiment.

FIG. 2A illustrates a part of the transducer elements included in the ultrasound probe 1. The following explains a reception signal based on a reflected-wave signal received by the one of the transducer elements (one of the channels [CH]) in FIG. 2A. FIG. 2B schematically illustrates an example of the reception signal based on the reflected-wave signal received by the one of the transducer elements (the one of the channels [CH]) illustrated in FIG. 2A. Further, FIG. 2B illustrates the reception signal of each of the two times at which an ultrasound wave is transmitted.

In FIG. 2B, it is assumed that the parts where the amplitude of the RF signal is large correspond to saturation in the A/D converter. On the assumption that the reflecting member is completely stationary, a packet data sequence A at an observation point X1 is always a saturated signal sequence. In other words, the signal of the packet data sequence A is a Direct Current (DC) signal from which white noise has disappeared due to the saturation. Similarly, on the assumption that the reflecting member is completely stationary, a packet data sequence B at an observation point X2 is an unsaturated signal sequence containing white noise. In contrast, when the patient's body moves, both the signal of the data sequence A and the signal of the data sequence B are present in a mixed manner. In that situation, it means that the saturated signal from which the white noise has disappeared and the unsaturated signal containing the white noise are both present in a mixed manner in the data sequences. Accordingly, the ratio of noise (N) to the signals (S) becomes lower. In other words, it is possible to speculate the degree of saturation of the reflected-wave signals on the basis of a relationship between the signals and the noise in the data sequences. In this manner, by examining the relationship between the signals and the noise in the data sequences observed after the beam forming process, the ultrasound diagnosis apparatus is configured to speculate the saturation of the CH signals observed before the beam forming process.

The medical image processing method described above is realized as a result of the Doppler processing circuitry 14 executing the correlation matrix calculating function 141, the calculating function 142, the MTI filter processing function 143, the speculating function 144, the block separating function 145, and the region combining function 146.

Figure 3:
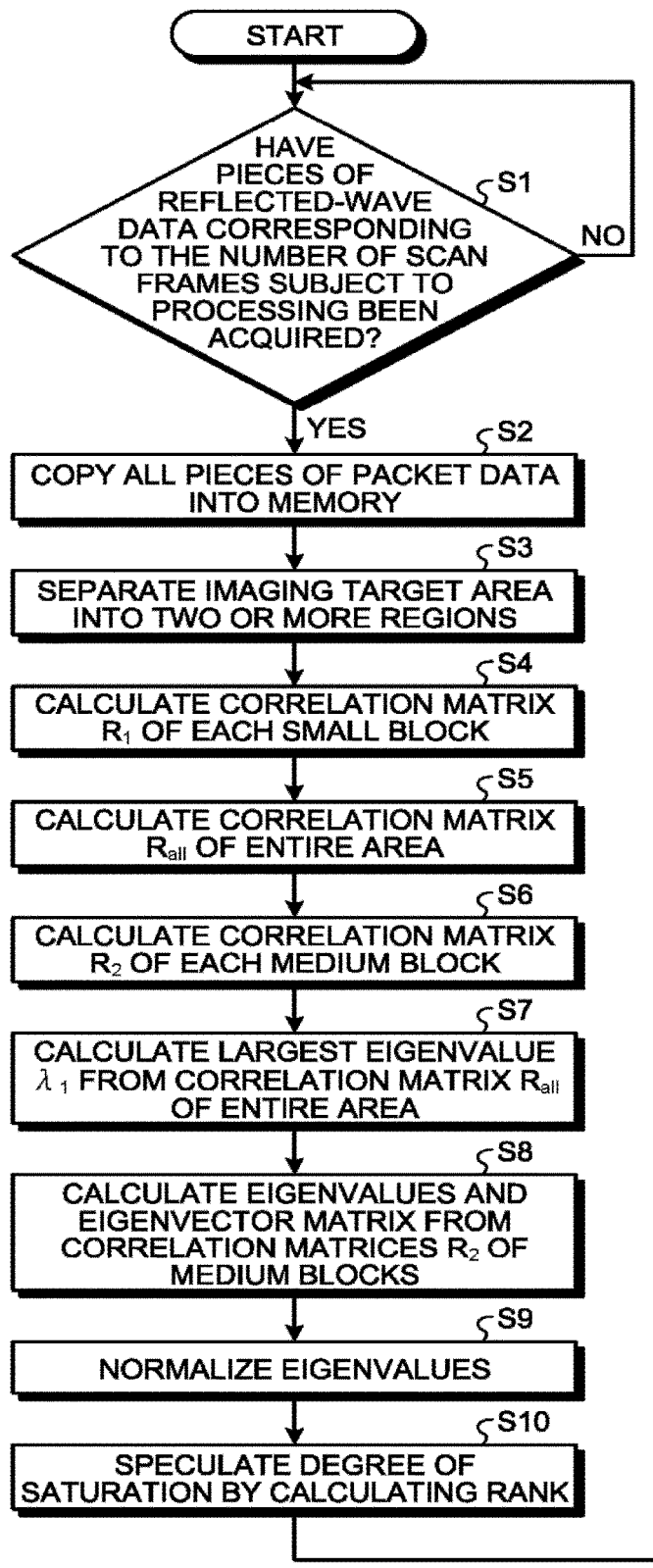
FIG. 3 is a flowchart illustrating a processing procedure performed by an ultrasound diagnosis apparatus according to the first embodiment.
Figure 3:
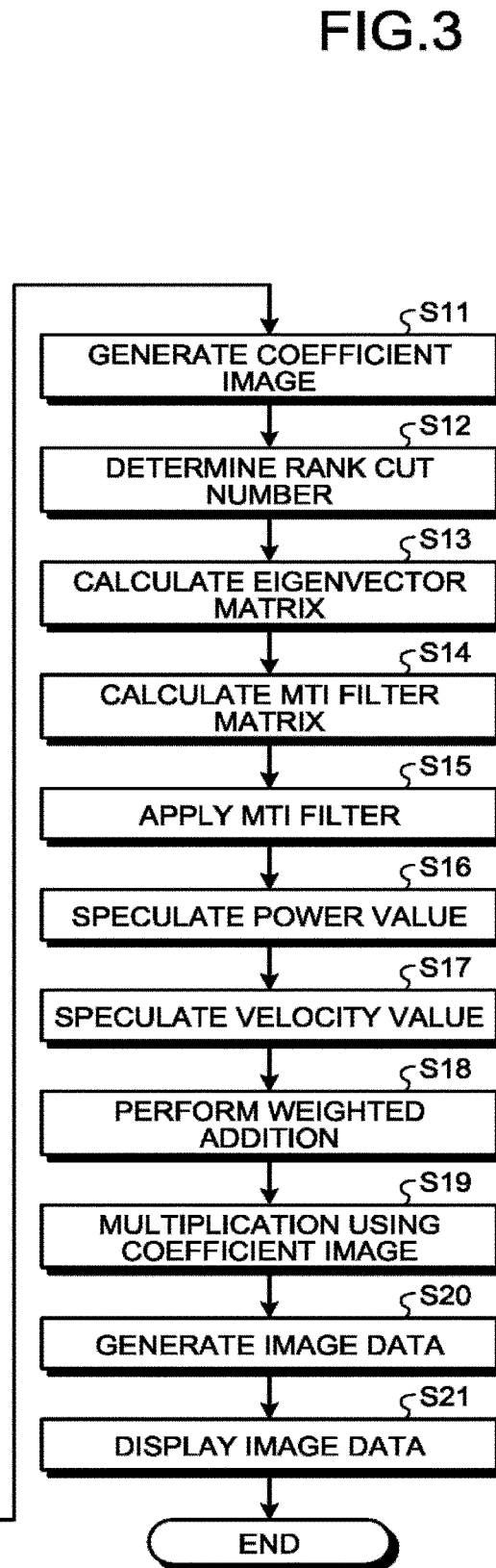

FIG. 3 is a flowchart illustrating a processing procedure performed by the ultrasound diagnosis apparatus according to the first embodiment. With reference to FIG. 3, which step in the flowchart corresponds to each of the constituent elements of the ultrasound diagnosis apparatus will be explained.

Steps S1 through S3 are steps corresponding to the block separating function 145. Steps S1 through S3 are steps at which the block separating function 145 is realized as a result of the Doppler processing circuitry 14 invoking and executing a predetermined program corresponding to the block separating function 145 from the internal storage circuit 17. At step S1, the block separating function 145 judges whether or not pieces of reflected-wave data corresponding to the number of scan frames subject to the processing have been acquired (step S1). In this situation, when having determined that the pieces of reflected-wave data corresponding to the number of scan frames have not been acquired (step S1: No), the block separating function 145 repeatedly performs the judging process at step S1.

On the contrary, when having determined that the pieces of reflected-wave data corresponding to the number of scan frames have been acquired (step S1: Yes), the block separating function 145 proceeds to step S2. At step S2, the block separating function 145 copies all the pieces of packet data corresponding to all the spatial points into a memory. In this situation, the number of all the spatial points will be expressed as N, whereas the packet size will be expressed as L. For example, the block separating function 145 copies the input data within the buffer 12 into a memory provided within the Doppler processing circuitry 14. The block separating function 145 performs the abovementioned copying operation for each invoked packet.

Figure 4:
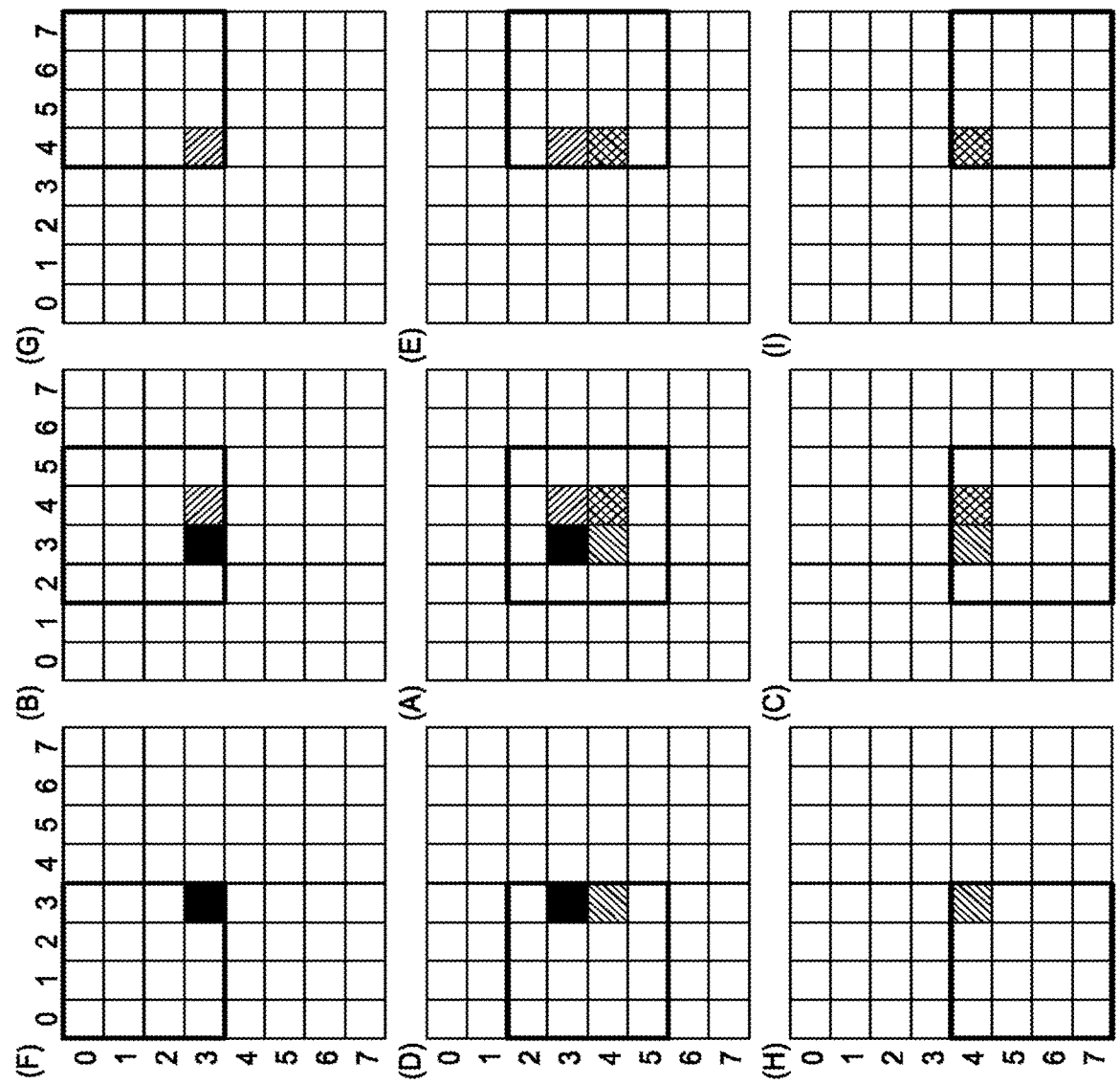
FIG. 4 is yet another drawing for explaining the first embodiment.

At step S3, the block separating function 145 separates an imaging target area into two or more regions. FIG. 4 is yet another drawing for explaining the first embodiment. FIG. 4 illustrates a partial region of the entire imaging target area. Further, FIG. 4 illustrates examples of mutually the same region in which the region is separated by using nine separation patterns (A) to (I).

For example, the block separating function 145 separates the imaging target area into the two or more regions, by using the small squares in FIG. 4 as the smallest separation units. The smallest separation units will be referred to as small blocks. In patterns (A) to (I) in FIG. 4, the separation patterns of the small blocks are mutually the same. In one example, the block separating function 145 separates the area so that each of the small blocks contains eight rasters and eight samples. In this situation, the block separating function 145 separates the spatial region into the small blocks so that there are a sufficient number of spatial samples for ensuring a certain degree of freedom (≥the packet length L).

Further, the block separating function 145 forms medium blocks, by using two or more of the small blocks for each medium block. For example, the block separating function 145 forms each of the medium blocks by putting together sixteen small blocks, four across and four down, enclosed in the bold frame indicated in FIG. 4. In other words, each of the medium blocks is formed by 4×4 small blocks. In one example, the block separating function 145 forms each of the medium blocks as illustrated in patterns (A) to (I) in FIG. 4.

Next, an example will be explained by using the medium block enclosed in the bold frame in pattern (A) in FIG. 4. The medium block in (A) overlaps with the medium blocks in some of patterns (B) to (I) that are positioned adjacent to pattern (A). For example, the solid black small block in pattern (A) is also contained, in a duplicate manner, as a solid black small block in each of the medium blocks in patterns (B), (D), and (F). In this manner, all the locations are contained in four mutually-different medium blocks in a duplicate manner. In other words, the block separating function 145 separates the imaging target area into the regions, in such a manner that a part of each of the regions overlaps with a part of at least one of the other regions.

Steps S4 through S6 are steps corresponding to the correlation matrix calculating function 141. Steps S4 through S6 are steps at which the correlation matrix calculating function 141 is realized as a result of the Doppler processing circuitry 14 invoking and executing a predetermined program corresponding to the correlation matrix calculating function 141 from the internal storage circuit 17. At step S4, the correlation matrix calculating function 141 calculates a correlation matrix $R_1$ in each of the small blocks. When a packet data column vector at a certain location point i is expressed as $x_i$, it is possible to express the correlation matrix $R_1$ by using Expression (1) presented below. In Expression (1), i denotes the position of the certain location point. (The single subscript i denotes the position of x,z for a two-dimensional scan and the position of x,y,z for a three-dimensional scan.) N denotes the number of location points used for the calculation. H denotes a complex conjugate transpose matrix (a Hermitian transpose matrix). When the packet length is expressed as L, $R_1$ is a matrix of L×L.

$$R_1 = \frac{1}{N}\sum_{i=1}^{N} x_i x_i^H \quad (1)$$

At step S5, the correlation matrix calculating function 141 calculates a correlation matrix $R_{all}$ of the entire area, by calculating an arithmetic mean of the correlation matrices of all the small blocks. When the total number of small blocks is expressed as $M_{all}$, it is possible to express the correlation matrix $R_{all}$ by using Expression (2) presented below.

$$R_{all} = \frac{1}{M_{all}}\sum_{m=1}^{M_{all}} R_{1,m} \quad (2)$$

At step S6, the correlation matrix calculating function 141 calculates a correlation matrix $R_2$ of each of the medium blocks. For example, when the correlation matrix of an m-th small block is expressed as $R_{1,m}$, whereas the number of small blocks to be added together is expressed as $M_2$, the correlation matrix calculating function 141 calculates $R_2$ by using Expression (3) presented below.

$$R_2 = \frac{1}{M_2}\sum_{m=1}^{M_2} R_{1,m} \quad (3)$$

More specifically, the correlation matrix calculating function 141 calculates the correlation matrix of each of the medium blocks formed by 4×4 small blocks. Even more specifically, the correlation matrix calculating function 141 calculates the correlation matrix of each of the medium blocks by adding together the correlation matrices calculated for the small blocks. In this situation, after calculating the correlation matrix of each of the medium blocks by adding together the correlation matrices calculated for the small blocks, the correlation matrix calculating function 141 divides the correlation matrix of each of the medium blocks by the total number N of pieces of spatial data in the medium block. In other words, the correlation matrix calculating function 141 calculates the correlation matrix $R_2$ of each of the medium blocks by calculating an arithmetic mean of the correlation matrices $R_1$ of the small blocks in the medium block.

Steps S7 through S13 are steps corresponding to the calculating function 142. Steps S7 through S13 are steps at which the calculating function 142 is realized as a result of the Doppler processing circuitry 14 invoking and executing a predetermined program corresponding to the calculating function 142 from the internal storage circuit 17. At step S7, the calculating function 142 calculates the largest eigenvalue $\lambda_1$ from the correlation matrix $R_{all}$ of the entire area. More specifically, the calculating function 142 performs an eigenvalue decomposition on $R_{all}$, by using Expression (4) presented below.

$$R_{all} = VDV^H \quad (4)$$

In Expression (4) above, V denotes a matrix having eigenvectors as the column vectors thereof. D denotes a diagonal matrix having eigenvalues as diagonal elements thereof. It is assumed that the eigenvalues $\lambda$ and eigenvectors corresponding to the eigenvalues $\lambda$ are each arranged in descending order. The matrix V can be expressed by using Expression (5) presented below. The matrix D can be expressed by using Expression (6) presented below. The calculating function 142 determines the largest eigenvalue in the matrix D to be $\lambda_1$.

$$V = \begin{pmatrix} v_{1,1} & v_{1,2} & \cdots & v_{1,L} \\ v_{2,1} & v_{2,2} & & v_{2,L} \\ \vdots & & & \vdots \\ v_{L,1} & v_{L,2} & \cdots & v_{L,L} \end{pmatrix} \quad (5)$$

$$D = \begin{pmatrix} \lambda_1 & 0 & \cdots & 0 \\ 0 & \lambda_2 & & 0 \\ \vdots & & \ddots & \vdots \\ 0 & 0 & \cdots & \lambda_L \end{pmatrix} \quad (6)$$

At step S8, the calculating function 142 calculates eigenvalues and the eigenvector V from the correlation matrix $R_2$ of each of the medium blocks. In this situation, the calculating function 142 calculates the eigenvalues and the eigenvectors from the correlation matrix of each of the medium blocks, in the same manner as at step S7 in FIG. 3.

At step S9, the calculating function 142 normalizes the eigenvalues. For example, the calculating function 142 normalizes, for each of the medium blocks, the eigenvalue $\lambda$ of $R_2$ by using a total power of the correlation matrix $R_{all}$ of the entire area (the sum of all the eigenvalues in $R_{all}$). As a result, it is possible to eliminate impacts of gains. In this situation, instead of performing the normalizing process by using the total power, the calculating function 142 may perform the normalizing process by using the largest eigenvalue $\lambda_1$ of $R_{all}$.

At step S10, the calculating function 142 speculates the degree of saturation by calculating rank. In the following sections, it is assumed that the rank is calculated in the following manner: When an eigenvalue $\lambda_i$ (where i=1 to L) among the eigenvalues that are normalized and arranged in descending order with respect to the correlation matrix $R_2$ of a medium block is the first to become equal to or smaller than a threshold value Th1, for example, the calculating function 142 defines i−1 as the rank of the correlation matrix $R_2$ of the medium block. Further, when all the eigenvalues are larger than Th1, the rank of the correlation matrix $R_2$ of the medium block is expressed as "L" and is referred to as "full rank".

After that, the calculating function 142 speculates the degree of saturation of the reflected-wave signals observed before the phased addition process, by defining a relationship between the signals and the noise by performing a statistical calculation while using the correlation matrices of the data sequence. More specifically, the calculating function 142 defines the signals by using one selected from among a total sum of the eigenvalues, the largest eigenvalue, and a high-rank eigenvalue and defines the noise by using one or more eigenvalues equal to or smaller than a threshold value.

In relation to this, with respect to dynamic ranges and white noise levels of electronic circuits used in currently-available ultrasound diagnosis apparatuses, when the eigenvalues are calculated by using a single-precision calculation, the result indicates full rank. However, the inventors of the present disclosure have discovered that, when the CH signals are saturated due to an echo from a powerful reflecting member, the correlation matrix is not full rank. Accordingly, the calculating function 142 speculates the saturation of the CH signals observed before the beam forming process, by examining the rank of the correlation matrix observed after the beam forming process.

Figure 5:
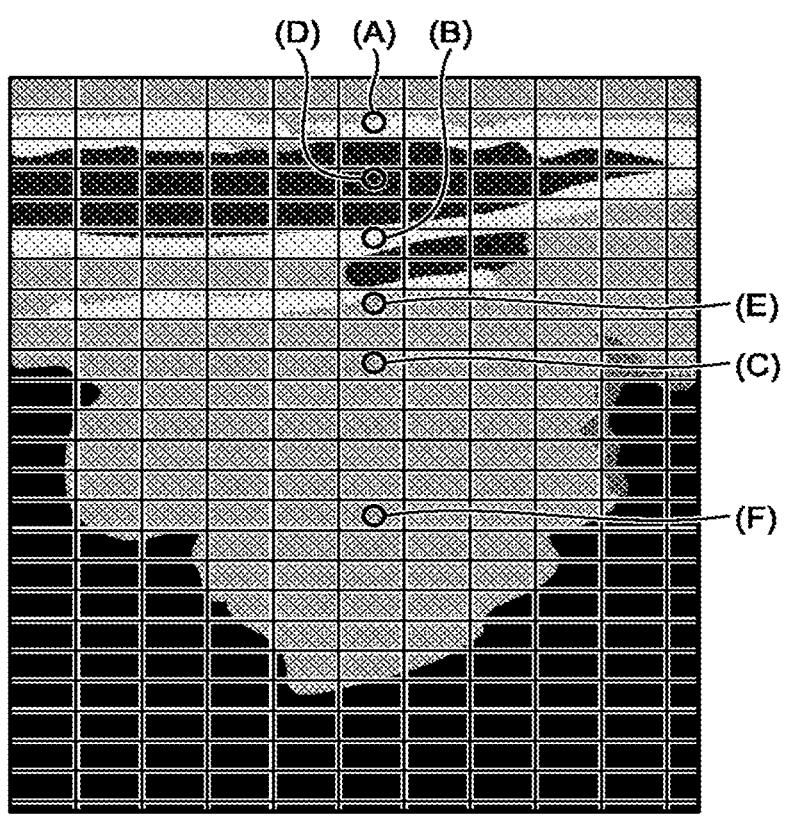
FIG. 5 is yet another drawing for explaining the first embodiment.
Figure 6:
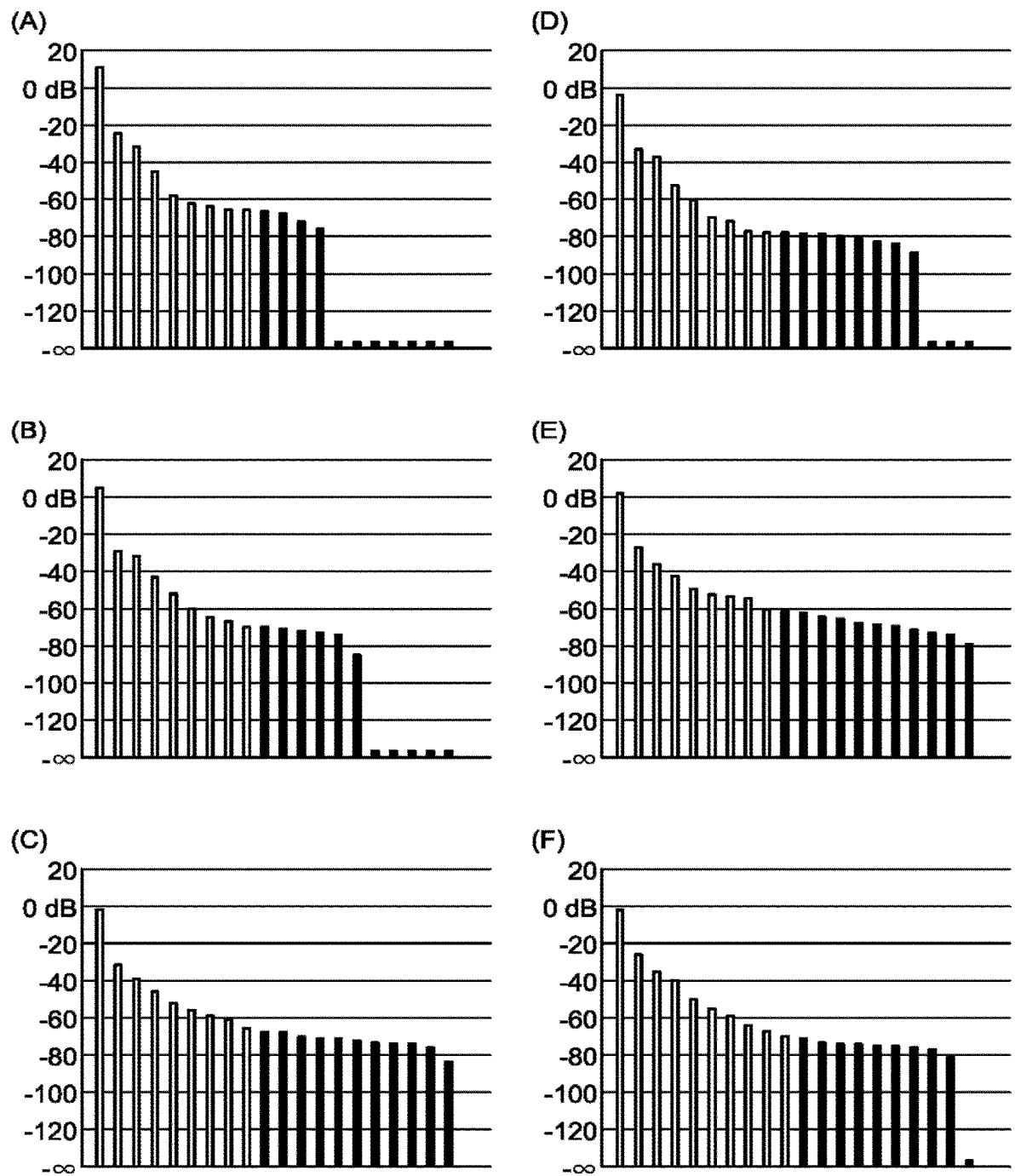
FIG. 6 is yet another drawing for explaining the first embodiment.

The following sections will explain the reason why it is possible to speculate the saturation of the CH signals observed before the beam forming process, by examining the rank of the correlation matrix observed after the beam forming process. FIGS. 5 and 6 are drawings for explaining the first embodiment. FIG. 5 illustrates an example of a B-mode image obtained by scanning the thyroid gland while using a linear probe. Further, in FIG. 5, each of the regions defined by the lines extending lengthwise and widthwise corresponds to a region of 2×2 small blocks positioned at the center of a medium block. Further, FIG. 5 illustrates six blocks (A) to (F) having mutually-different degrees of brightness.

FIG. 6 illustrates eigenvalues of the correlation matrix of each of the six blocks (A) to (F) illustrated in FIG. 5. The eigenvalues of the correlation matrices of (A) to (F) in FIG. 6 correspond to the blocks (A) to (F) in FIG. 5. In the example in FIG. 6, because L=20 is satisfied, the rank number of the full rank is 20. In FIG. 6, the rank is 13 for block (A); the rank is 15 for block (B); the rank is 20 for block (C); the rank is 17 for block (D); the rank is 20 for block (E); and the rank is 19 for block (F).

In the B-mode image illustrated in FIG. 5, blocks (A) and (B) have higher degrees of brightness. In other words, in blocks (A) and (B), the amplitude observed after the beam forming process is larger, and there is a possibility that the CH signals may be saturated. Further, the rank is 13 in block (A), whereas the rank is 15 in block (B). As observed herein, for example, blocks (A) and (B) having higher degrees of brightness in the B-mode image in FIG. 5 do not exhibit full rank, as indicated in FIG. 6.

Next, the following will explain a relationship between rank deficiency of correlation matrices observed after the beam forming process and saturation of the signals of the channels [CH] observed before the beam forming process. For example, it is possible to express a correlation calculation between two frames with respect to a sum of signals a and b of two channels [CH] (channels CHa and CHb) by using Expression (7) presented below. In Expression (7), the symbol "*" denotes the complex conjugate of each of the elements in the matrix.

$$\begin{pmatrix} a_1 + b_1 \\ a_2 + b_2 \end{pmatrix}(a_1 + b_1 \ a_2 + b_2)^* = \\ \begin{pmatrix} a_1 \\ a_2 \end{pmatrix}(a_1 \ a_2)^* + \begin{pmatrix} b_1 \\ b_2 \end{pmatrix}(b_1 \ b_2)^* + \begin{pmatrix} a_1 \\ a_2 \end{pmatrix}(b_1 \ b_2)^* + \begin{pmatrix} b_1 \\ b_2 \end{pmatrix}(a_1 \ a_2)^* \quad (7)$$

In Expression (7), the first term and the second term on the right-hand side are each an autocorrelation matrix, whereas the third term and the fourth term on the right-hand side are each a cross-correlation matrix. In other words, it is possible to express Expression (7) as a sum of the autocorrelation matrices of the channels [CH] and the cross-correlation matrices among the channels [CH]. In this situation, because the first and the second terms are each a linear term, the third and the fourth terms will be discussed. The signals a and b are signals resulting from the application of the mutually-different delays for the purpose of matching the phases during the phased adding process. Accordingly, when only the main lobe is taken into consideration, the cross-correlation between the signal a and the signal b is strong. Because a signal having larger amplitude has a stronger impact in correlation matrices, it is sufficient to take only the main lobe into consideration. For this reason, when the signal a is saturated, it is considered that there is a high possibility that the signal b is also saturated. In contrast, with respect to white noise, the cross-correlation between the signals a and b is 0.

Consequently, from the viewpoint where the S/N value increases when saturation occurs, it is safe to say that the correlation matrix obtained by performing a phased adding process on the signals a and b is the same as the sum of the correlation matrix of the signal a and the correlation matrix of the signal b. In other words, when a correlation matrix observed after the beam forming process is rank deficient, it is possible to speculate that the signals of one or more channels [CH] observed before the beam forming process are saturated. In this manner, the calculating function 142 speculates the saturation of the CH signals observed before the beam forming process, on the basis of the rank of the correlation matrices observed after the beam forming process.

More specifically, the calculating function 142 speculates the degree of saturation of the CH signals in the region, in accordance with the rank calculated for each of the medium blocks. For example, the calculating function 142 speculates that the degree of saturation is lower when the rank is closer to full rank and that the degree of saturation is higher when the rank is closer to 1. In this manner, the calculating function 142 speculates the degree of saturation in each of the sectional regions by performing the statistical calculation on the basis of the data sequence of the sectional region, the sectional regions having been obtained by separating the scan range formed with the plurality of scanning lines into two or more regions.

Returning to the description of FIG. 3, at step S11, the calculating function 142 generates a coefficient image. For example, the calculating function 142 generates a coefficient image C0 obtained by entering, at the center of each medium block, "1" serving as an output value when the medium block is full rank and a coefficient "α" being smaller than 1 and serving as an output value when the medium block is not full rank. In other words, the calculating function 142 generates the coefficient image C0 as data based on the result of the saturation speculating process.

In this situation, the calculating function 142 may vary the value of the coefficient α depending on the value of the rank, as indicated in Expression (8) below, where β<1 is satisfied. When the rank is full rank (Rank=L), α=1 is satisfied. When the rank is deficient, α<1 is satisfied. In other words, for example, when the rank of the correlation matrix of a data sequence is not full rank, the calculating function 142 speculates that the degree of saturation is equal to or higher than a threshold value.

$$\alpha = \beta^{(L-Rank)} \quad (8)$$

Figure 7:
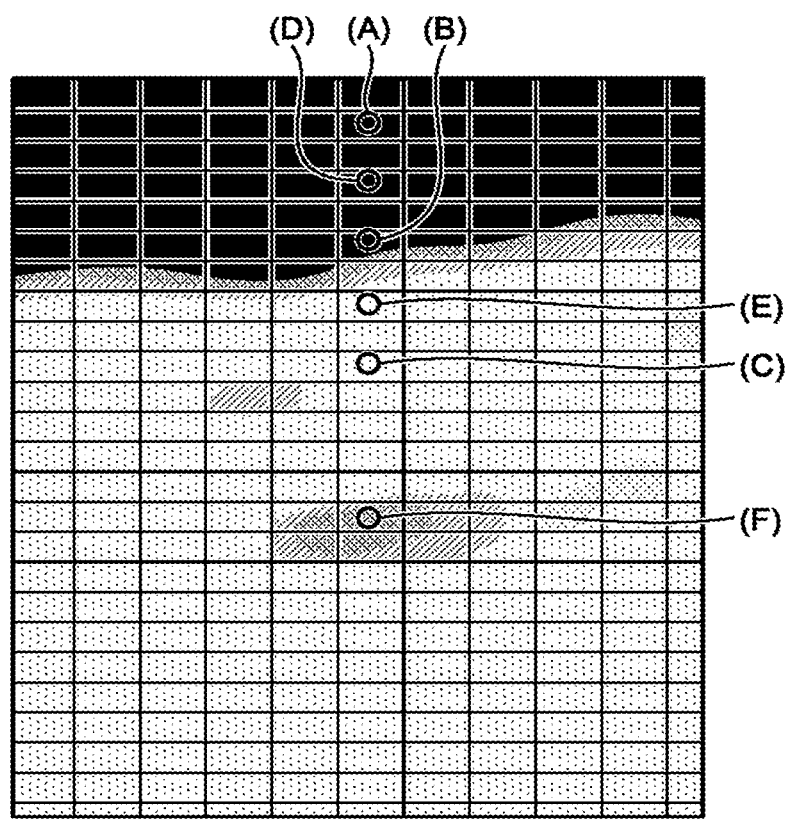
FIG. 7 is yet another drawing for explaining the first embodiment.

Further, the calculating function 142 generates a coefficient image C1 as illustrated in FIG. 7, for example, by enlarging the coefficient image C0 by interpolating the coefficient image C0 into the entire image region. In this manner, the calculating function 142 generates correction information from the result of the speculation. Blocks (A) to (F) in FIG. 7, correspond to blocks (A) to (F) in FIG. 5. FIG. 7 is yet another drawing for explaining the first embodiment.

At step S12, the calculating function 142 calculates an optimal rank cut number k from the eigenvalues. For example, the calculating function 142 may calculate the optimal rank cut number k for each of the medium blocks by using a method disclosed in Patent Literature 1 (Japanese Patent Laid-open No. 2014-158698) or as the smallest value that makes $\lambda_k$ equal to or smaller than a threshold value. By performing the normalizing process with the largest eigenvalue in the correlation matrix of the entire image in this manner, it is possible to eliminate gain dependency and impacts of differences among tissues in the patient's body caused by the region separating process.

At step S13, by using the value of k (where k≤L) calculated above, the calculating function 142 calculates an eigenvector matrix $V_k$ (an L×K matrix) of which the rank number is k. In this situation, it is possible to express the eigenvector matrix $V_k$ by using Expression (9) presented below.

$$V_k = \begin{pmatrix} v_{1,1} & v_{1,2} & \cdots & v_{1,k} \\ v_{2,1} & v_{2,2} & & v_{2,k} \\ \vdots & & & \vdots \\ v_{L,1} & v_{L,2} & \cdots & v_{L,k} \end{pmatrix} \quad (9)$$

At step S14, the calculating function 142 calculates an MTI filter matrix W from $V_k$. In Expression (10), I denotes a unit matrix of L×L.

$$w = I - V_k V_k^H \quad (10)$$

Step S15 is a step corresponding to the MTI filter processing function 143. Step S15 is a step at which the MTI filter processing function 143 is realized as a result of the Doppler processing circuitry 14 invoking and executing a predetermined program corresponding to the MTI filter processing function 143 from the internal storage circuit 17. At step S15, the MTI filter processing function 143 applies an MTI filter to the packet column vector data $x_i$ at each of the points by using Expression (11) presented below.

$$y_i = W x_i \quad (11)$$

For example, the MTI filter processing function 143 applies an MTI filter calculated from the data of a medium block in (A) formed by 4×4 small blocks, to the data of the medium block in (A) formed by the 4×4 small blocks.

Steps S16 and S17 are steps corresponding to the speculating function 144. Steps S16 and S17 are steps at which the speculating function 144 is realized as a result of the Doppler processing circuitry 14 invoking and executing a predetermined program corresponding to the speculating function 144 from the internal storage circuit 17. At steps S16 and S17, the speculating function 144 extracts moving member information by performing the statistical calculation on the basis of the data sequence. For example, the speculating function 144 extracts the moving member information of each of the sectional regions by using a statistical characteristic calculated from the sectional region, the sectional regions having been obtained by separating the scan range formed with the plurality of scanning lines into two or more regions.

More specifically, at step S16, the speculating function 144 speculates a power value P by using Expression (12) presented below, on the basis of the data of the medium block to which the MTI filter was applied at step S15. In this situation, the speculating function 144 speculates the power value P as a value before a logarithmic compression. In Expression (12), j denotes an index indicating an element number of the column vector.

$$P_i = \sum_{j=1}^{L} |y_{i,j}|^2 \quad (12)$$

Further, at step S17, the speculating function 144 speculates a velocity value V by using Expression (13) presented below, on the basis of the data of the medium block to which the MTI filter was applied at step S15. In Expression (13), "angle" denotes a mathematical function used for outputting the argument of a complex number in the range from −π to π.

$$V_i = \text{angle}\left(\sum_{j=1}^{L-1} y_{i,j}^* y_{i,j+1}\right) \quad (13)$$

In this situation, the speculating function 144 may perform the processes at steps S16 and S17 in the reverse order or at the same time.

Figure 8:
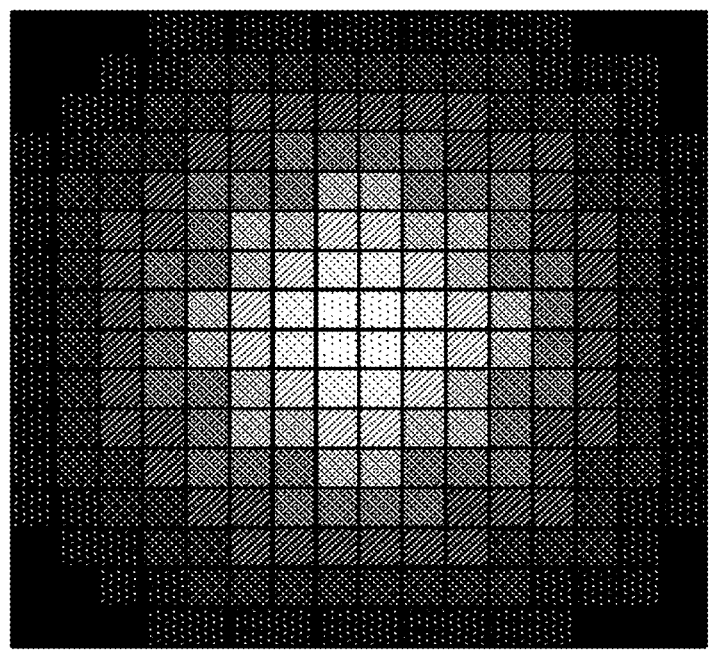
FIG. 8 is yet another drawing for explaining the first embodiment.

Steps S18 and S19 are steps corresponding to the region combining function 146. Steps S18 and S19 are steps at which the region combining function 146 is realized as a result of the Doppler processing circuitry 14 invoking and executing a predetermined program corresponding to the region combining function 146 from the internal storage circuit 17. At step S18, the region combining function 146 performs a weighted addition process. For example, the region combining function 146 performs a region combining process for the power values and a region combining process for the velocity values. FIG. 8 is yet another drawing for explaining the first embodiment. FIG. 8 illustrates a distribution of weights corresponding to different positions. For example, the region combining function 146 interpolates pixels by performing multiplication with weight coefficients corresponding to the different positions while implementing a bi-linear method that uses the weight coefficients illustrated in FIG. 8 and performing addition using the data in the same position.

At step S19, the region combining function 146 multiplies the coefficient image generated at step S11 by the power value speculated at step S16. In other words, when the degree of saturation is speculated to be equal to or higher than a threshold value, the region combining function 146 corrects the moving member information. For example, the region combining function 146 extracts a power value as the moving member information and suppresses the extracted power value. More specifically, the region combining function 146 corrects the moving member information by using the correction information.

Step S20 is a step realized by the image generating circuit 15. At step S20, the image generating circuit 15 generates color Doppler image data from the moving member information. For example, the image generating circuit 15 generates the color Doppler image data by performing a logarithmic compression on the power value P speculated at step S16. Further, the image generating circuit 15 generates color Doppler image data based on the velocity value V speculated at step S17.

Step S21 is a step realized by the processing circuitry 18. At step S21, the processing circuitry 18 causes the display 2 to display the color Doppler image data.

Figure 9A:
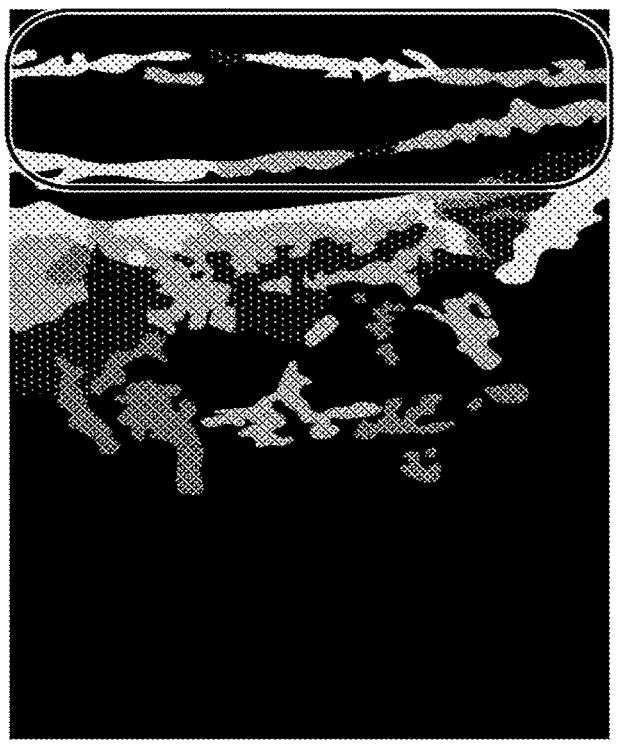
FIG. 9A is yet another drawing for explaining the first embodiment.
Figure 9B:
FIG. 9B is yet another drawing for explaining the first embodiment.
Figure 9C:
FIG. 9C is yet another drawing for explaining the first embodiment.

FIGS. 9A to 9C are other drawings for explaining the first embodiment. FIGS. 9A to 9C illustrate an example of a blood flow in the thyroid gland. FIG. 9A illustrates an example of an image obtained by applying mutually the same single MTI filter to the entire image without performing the region separating process. FIG. 9B illustrates an example of an image obtained by performing the region separating process and applying an appropriate one of mutually-different MTI filters to each of the regions. FIG.

9C illustrates an example of an image obtained according to the first embodiment. In FIG. 9A, the tissue is overall visible, and the tissue is significantly visible in the region marked with the rounded rectangle. In FIG. 9B, a boundary tissue of the body surface muscle layer, which is indicated with the rounded rectangle, is visible. In FIG. 9C, the tissues in the positions that are visible in the rounded rectangles in FIGS. 9A and 9B are not at all visible.

As explained above, the ultrasound diagnosis apparatus according to the first embodiment is configured to speculate saturation at each of the observation points, on the basis of the relationship between the signals and the noise in the data sequence represented by the set made up of pieces of reflected-wave data generated by the phased addition process and is configured to correct the moving member information by using the correction information generated from the result of the speculation. For example, the ultrasound diagnosis apparatus according to the first embodiment is configured to lower the gain by speculating the degree of saturation. As a result, according to the first embodiment, by using the IQ signals observed after the beam forming process, it is possible to avoid the problem where an artifact is displayed as if a blood flow was present, when the CH signals observed before the beam forming process become saturated due to a powerful reflecting member, during the implementation of the blood flow imaging method that uses the adaptive MTI filter employing the eigenvectors.

Further, it is confirmed that the ultrasound diagnosis apparatus according to the first embodiment is able to reduce artifacts caused by a powerful reflecting member, even when no saturation is involved. For example, in the situation where the gain of the pre-amplifier is lowered, while the echo from a powerful reflecting member is not saturated in the A/D converter, and the white noise level is small, there is a possibility that, in some situations, the normalized eigenvalue may become equal to or smaller than the threshold value Th1 due to a large S/N value. Also, when a powerful reflecting member moves by a relatively large amount, the movement may become visible, in some situations, as a motion artifact as passing through the MTI filter, even if there is no saturation. Even in those situations, the first embodiment achieves an advantageous effect where the motion artifact from the powerful reflecting member is suppressed. In those situations, it is considered that a nonlinear effect is achieved where a part of the white noise becomes equal to or smaller than an observation limit level because of the lowering of the gain of the pre-amplifier. In other words, according to the first embodiment, when a signal having strong amplitude corresponding to saturation or equivalent to saturation is input to the signal observed before the beam forming process, it is possible to avoid the problem that is caused in the signal processing processes performed by using the signals observed after the beam forming process.

In the first embodiment described above, the block separating function 145 is configured to separate the imaging target area into the small blocks as illustrated in FIG. 4. Accordingly, the correlation matrix calculating function 141 is able to calculate the correlation matrix of each of the medium blocks, by adding together the correlation matrices of the small blocks. Further, because the medium blocks overlap with one another in units of small blocks, there is no waste in the calculations of the correlation matrices. Furthermore, by arranging the spatial data and the packet data to be stored in a memory in units of small blocks, it is possible to achieve excellent cache efficiency when a CPU executes the MTI filter matrix calculations.

Further, according to the first embodiment described above, the example is explained in which the block separating function 145 is configured to form the medium blocks in such a manner that a part of each of the medium blocks overlaps with a part of at least one other medium block; however, possible embodiments are not limited to this example. For instance, the block separating function 145 may form the medium blocks in such a manner that a part of each of the medium blocks does not overlap with a part of any other medium block.

Further, in the embodiments described above, the example is explained in which the speculating function 144 is configured to extract the moving member information from the data to which the MTI filter is applied, the MTI filter having been generated with respect to each of the regions obtained by separating the imaging target area into two or more regions; however, possible embodiments are not limited to this example. For instance, the speculating function 144 may extract the moving member information from data to which an MTI filter is applied, the MTI filter having been generated with respect to the entire imaging target area.

Further, in the embodiments described above, the example is explained in which the calculating function 142 is configured to speculate the degree of saturation by calculating the rank from the correlation matrices of the medium blocks; however, possible embodiments are not limited to this example. For instance, the calculating function 142 may speculate the degree of saturation by calculating the rank from a correlation matrix of the entire imaging target area.

Further, the rank of the correlation matrix of the measured values containing noise varies depending on the level of precision of the calculation. In other words, because the rank is determined by machine epsilon, the rank is dependent on the level of precision of the calculation. For example, while the CH signals were saturated, when the rank was calculated by performing the eigenvalue decomposition by using a single-precision calculation, the rank was found to be deficient, but when the rank was calculated by using a double-precision calculation, the rank was not found to be deficient. For the purpose of eliminating the dependency on the level of precision of the calculation, the normalized eigenvalues are compared with the threshold value Th1, so as to define the number of eigenvalues that are equal to or larger than the threshold value as the rank. By using this definition, the value of the rank will be substantially the same regardless of whether the single-precision calculation is used or the double-precision calculation is used, as long as the threshold value Th1 is set to an appropriate value. For this reason, when performing the single-precision calculation, the calculating function 142 may omit the eigenvalue normalizing process explained at step S9 in FIG. 3.

A Modification Examples of First Embodiment

In the first embodiment described above, the example is explained in which the Doppler processing circuitry 14 is configured to calculate the correlation matrix as a statistical characteristic and performs the eigenvalue decomposition. As a modification example of the first embodiment, an example will be explained in which, instead of calculating the correlation matrix, a singular value decomposition is performed on a matrix $X^H$ to obtain a statistical characteristic. For example, when the number of all the spatial points is expressed as N, while the packet size is expressed as L, it is possible to express Expression (2) presented above with Expression (14) presented below, by using a matrix X of L×N where the column vectors of the matrix X are $x_i$.

$$R_1 = \frac{1}{N} XX^H \quad (14)$$

The Doppler processing circuitry 14 performs a singular value decomposition on the matrix $X^H$, by using Expression (15) presented below.

$$X^H = P\Lambda Q^H \quad (15)$$

When Expression (15) is assigned to Expression (14), because P is a unitary matrix, it is possible to express $R_1$ by using Expression (16) presented below.

$$R_1 = \frac{1}{N} XX^H = \frac{1}{N}(P\Lambda Q^H)^H(P\Lambda Q^H) = \frac{1}{N} Q\Lambda^H P^H P\Lambda Q^H = \frac{1}{N} Q\Lambda^H \Lambda Q^H \quad (16)$$

When Expression (4) is compared with Expression (16), it is possible to express V by using Expression (17) presented below and to express D by using Expression (18) presented below.

$$V = Q \quad (17)$$

$$D = \frac{1}{N} \Lambda^H \Lambda \quad (18)$$

In Expression (18), $\Lambda$ is a matrix of N×L, while the eigenvalues of the Hermitian matrix $R_1$ are positive. Accordingly, it is possible to express $\Lambda$ by using Expression (19) presented below.

$$\Lambda = \sqrt{N} \begin{pmatrix} \sqrt{\lambda_1} & 0 & \cdots & 0 \\ 0 & \sqrt{\lambda_2} & & 0 \\ \vdots & & \ddots & \vdots \\ 0 & 0 & \cdots & \sqrt{\lambda_L} \\ 0 & 0 & \cdots & 0 \\ \vdots & \vdots & \ddots & \vdots \\ 0 & 0 & \cdots & 0 \end{pmatrix} \quad (19)$$

Further, the calculating function 142 defines the signals by using one selected from among a total sum of singular values, the largest singular value, and a high-rank singular value and defines the noise by using a singular value equal to or smaller than a threshold value.

In that situation, the MTI filter processing function 143 applies an MTI filter to the packet column vector data X of each of the points, by using Expression (20) presented below.

$$Y = WX \quad (20)$$

As explained above, according to the modification example of the first embodiment, the Doppler processing circuitry 14 speculates the degree of saturation by performing the singular value decomposition on the matrix $X^H$ instead of calculating the correlation matrices.

Second Embodiment

In the first embodiment, the example is explained in which, when the color Doppler image data is to be generated as the data based on the result of the signal saturation speculating process, the moving member information is extracted by using the eigenvector MTI filter. Incidentally, when the CFM method is implemented, moving member information may be extracted in some situations by using a filter having a fixed coefficient as the MTI filter. The embodiment is also applicable to those situations. Accordingly, as a second embodiment, an example will be explained in which, when color Doppler image data is to be generated as data based on a result of the signal saturation speculating process, moving member information is extracted by using a filter having a fixed coefficient as the MTI filter.

An exemplary configuration of an ultrasound diagnosis apparatus according to the second embodiment is the same as the exemplary configuration of the ultrasound diagnosis apparatus according to the first embodiment illustrated in FIG. 1, except that a part of the processing procedure performed by the MTI filter processing function 143 is different. For this reason, in the second embodiment, only the MTI filter processing function 143 will be explained.

FIG. 10 is a flowchart illustrating a processing procedure performed by the ultrasound diagnosis apparatus according to the second embodiment. With reference to FIG. 10, which step in the flowchart corresponds to each of the constituent elements of the ultrasound diagnosis apparatus will be explained. In the flowchart in FIG. 10, some of the processes that are the same as those in the flowchart in FIG. 3 will be referred to by using the same reference numbers, and detailed explanations thereof will be omitted. For example, the processes at steps S31 through S41 illustrated in FIG. 10 correspond to the processes at steps S1 through S11 illustrated in FIG. 3.

Steps S42 and S43 are steps corresponding to the MTI filter processing function 143. Steps S42 and S43 are steps at which the MTI filter processing function 143 is realized as a result of the Doppler processing circuitry 14 invoking and executing a predetermined program corresponding to the MTI filter processing function 143 from the internal storage circuit 17. At step S42, the MTI filter processing function 143 sets a cut-off frequency. For example, when the degree of saturation is speculated to be equal to or higher than a threshold value, the MTI filter processing function 143 raises the cut-off frequency of the filter used for extracting the moving member information from the data sequence so as to be higher than a cut-off frequency used when the degree of saturation is lower than the threshold value. Subsequently, at step S43, the MTI filter processing function 143 applies an MTI filter to the data sequence. In this situation, the MTI filter processing function 143 applies the MTI filter of a fixed coefficient type designed for the entire imaging target area.

In this situation, the speculating function 144 extracts the moving member information from the data sequence to which the MTI filter was applied. In other words, when the degree of saturation is speculated to be equal to or higher than the threshold value, the speculating function 144 extracts the moving member information from the data sequence on which the MTI filter processing process was performed while raising the cut-off frequency of the filter used for extracting the moving member information from the data sequence so as to be higher than the cut-off frequency used when the degree of saturation is lower than the threshold value. After that, the image generating circuit 15 generates image data based on the moving member information.

As explained above, in the second embodiment, the degree of saturation is speculated, and the cut-off frequency is set in accordance with the degree of saturation. As a result, according to the second embodiment, it is possible to improve the image quality while implementing the CFM method.

Further, in the second embodiment described above, the example is explained in which the MTI filter processing function 143 is configured to apply the MTI filter of the fixed coefficient type designed for the entire imaging target area; however, possible embodiments are not limited to this example. For instance, the MTI filter processing function 143 may apply an MTI filter of a fixed coefficient type generated for each of the regions obtained by separating the imaging target area into two or more regions.

Further, in the second embodiment described above, the example is explained in which the calculating function 142 is configured to speculate the degree of saturation by calculating the rank from the correlation matrix of each of the medium blocks; however, possible embodiments are not limited to this example. For instance, the calculating function 142 may speculate the degree of saturation by calculating the rank from a correlation matrix of the entire imaging target area.

Third Embodiment

In the embodiments described above, the example is explained in which, while the CFM method is implemented, the blood flow image in which impacts of the saturated signals have been alleviated is generated, as the data based on the result of the signal saturation speculating process; however, possible embodiments are not limited to the example in which the blood flow image is generated. For example, the ultrasound diagnosis apparatus may be configured to generate evaluation-purpose image data, as data based on the result of the signal saturation speculating process.

An exemplary configuration of an ultrasound diagnosis apparatus according to a third embodiment is the same as the exemplary configuration of the ultrasound diagnosis apparatus according to the first embodiment illustrated in FIG. 1, except that a part of the processing procedure performed by the processing circuitry 18 is different. For this reason, in the third embodiment, only the processing circuitry 18 will be explained.

FIG. 11 is a flowchart illustrating a processing procedure performed by the ultrasound diagnosis apparatus according to the third embodiment. With reference to FIG. 11, which step in the flowchart corresponds to each of the constituent elements of the ultrasound diagnosis apparatus will be explained. In the flowchart in FIG. 11, some of the processes that are the same as those in the flowchart in FIG. 3 will be referred to by using the same reference numbers, and detailed explanations thereof will be omitted.

In the following sections, an example will be explained in which the processes illustrated in FIG. 11 are performed, for example, during an implementation of the CFM method by using data; however, it is also acceptable to perform the processes prior to the implementation of the CFM method or to perform the processes together with the implementation of the CFM method in a time-division manner. It is assumed that the scan range in the processes illustrated in FIG. 11 contains at least a part of the scan range on which the CFM method is implemented. Further, although the third embodiment will be explained on the assumption that an adaptive MTI filter is used as the MTI filter during the implementation of the CFM method, it is also acceptable to use a filter having a fixed coefficient as the MTI filter.

The processes at steps S51 through S68 and the process at step S69 illustrated in FIG. 11 correspond to the processes at steps S1 through S18 and the process at step S20 illustrated in FIG. 3, respectively. In other words, in FIG. 11, the process of correcting the moving member information performed by the region combining function 146 at step S19 in FIG. 3 is omitted.

The process at step S70 is a step realized by the processing circuitry 18. At step S70, the processing circuitry 18 causes the display 2 to display color Doppler image data and coefficient image data serving as the evaluation-purpose image data. Accordingly, an operator of the ultrasound diagnosis apparatus is able to check to see whether or not there is an observation point at which the reflected-wave signal is saturated in the ultrasound scan range. For example, when there is no observation point at which the reflected-wave signal is saturated, the operator is able to evaluate that the measured values obtained from the ultrasound scan are not impacted by saturation and therefore have high reliability. On the contrary, when there are one or more observation points at which the reflected-wave signals are saturated, the operator is able to evaluate that the measured values obtained from the ultrasound scan are impacted by the saturation and therefore have low reliability. In addition to using the reliability of the measured values for the assessment as to whether the image is correct or not, it is also possible to use the evaluation as an index for reliability of measured values to determine whether the measured values obtained by counting the number of pixels in a region where a blood flow is present to assess whether the blood flow is abundant or scarce are reliable or not.

As explained above, in the third embodiment, the coefficient image data is generated as the evaluation-purpose image data and is displayed on the display 2. Accordingly, it is possible to evaluate the reliability of the measured values. As a result, according to the third embodiment, it is possible to improve the image quality while implementing the CFM method.

Further, in the third embodiment described above, the example is explained in which the calculating function 142 generates the coefficient image data as the evaluation-purpose image data; however possible embodiments are not limited to this example. For instance, the calculating function 142 may generate text information and/or audio information indicating the degree of saturation, as the evaluation-purpose image data.

Further, in the third embodiment described above, the example is explained in which the processing circuitry 18 causes the display 2 to display the color Doppler image data and the coefficient image data serving as the evaluation-purpose image data; however, possible embodiments are not limited to this example. For instance, when the processes are performed prior to the implementation of the CFM method, the processing circuitry 18 may cause the display 2 to display only the coefficient image data, without causing the display 2 to display the color Doppler image data.

Other Embodiments

Possible embodiments are not limited to the embodiments described above.

In the embodiments described above, the example is explained in which the imaging target area is separated into the two or more regions, so as to speculate the saturation of the signals on the basis of the correlation matrix of each of the sectional regions; however, possible embodiments are not limited to this example. For instance, the ultrasound diagnosis apparatus may be configured to speculate saturation of the signals on the basis of the correlation matrix of the entire imaging target area. Further, in that situation, when implementing the CFM method, the ultrasound diagnosis apparatus may be configured to extract the moving member information by employing an MTI filter calculated from the correlation matrix of the entire imaging target area or may be configured to extract the moving member information by employing an MTI filter calculated from the correlation matrix of each of the sectional regions. Alternatively, when implementing the CFM method, the ultrasound diagnosis apparatus may be configured to extract the moving member information by employing an MTI filter having a fixed coefficient.

The term "processor" used in the explanation above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). Each of the processors realizes the functions thereof by reading and executing a corresponding one of the programs stored in a storage circuit. In this situation, instead of saving the programs in the storage circuit, it is also acceptable to directly incorporate the programs in the circuits of the processors. In that situation, each of the processors realizes the functions thereof by reading and executing the corresponding one of the programs incorporated in the circuit thereof. Further, the processors in the present embodiments do not each necessarily have to be structured as a single circuit. It is also acceptable to structure one processor by combining together a plurality of independent circuits so as to realize the functions thereof. Further, it is also acceptable to integrate two or more of constituent elements illustrated in FIG. 1 into a single processor so as to realize the functions thereof.

The constituent elements of the apparatuses and the devices illustrated in the drawings used in the explanations of the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program that is analyzed and executed by the CPU or may be realized as hardware using wired logic.

Further, the medical image processing methods explained in the above embodiments may be realized by causing a computer such as a personal computer or a workstation to execute a control program prepared in advance. The control program may be distributed via a network such as the Internet. Further, the control program may be recorded on a computer-readable recording medium such as a hard disk, a flexible disk (FD), Compact Disk Read-Only Memory (CD-ROM), a Magneto-Optical (MO) disk, or a Digital Versatile Disk (DVD), so as to be executed as being read from the recording medium by a computer.

According to at least one aspect of the embodiments described above, it is possible to improve the image quality while implementing the CFM method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising processing circuitry configured:
   to generate a piece of reflected-wave data by performing a phased addition process while using reflected-wave signals generated by transmitting an ultrasound wave with respect to a same scanning line and to estimate saturation of the reflected-wave signals observed before the phased addition process on a basis of a relationship between signals and noise in a data sequence represented by a set made up of pieces of the reflected-wave data;
   to output a result of the estimation; and
   to cause a display to display data based on the result of the estimation.

2. The ultrasound diagnosis apparatus according to claim 1, wherein the processing circuitry defines the relationship between the signals and the noise by performing a statistical calculation while using a correlation matrix of the data sequence and further estimates the saturation of the reflected-wave signals observed before the phased addition process.

3. The ultrasound diagnosis apparatus according to claim 2, wherein the processing circuitry estimates the saturation with respect to each of sectional regions by performing the statistical calculation on a basis of a data sequence of the sectional region, the sectional regions having been obtained by separating a scan range formed with a plurality of scanning lines into two or more regions.

4. The ultrasound diagnosis apparatus according to claim 2, wherein the processing circuitry defines the signals by using one selected from among a total sum of eigenvalues, a largest eigenvalue, and a high-rank eigenvalue and defines the noise by using one or more eigenvalues equal to or smaller than a threshold value.

5. The ultrasound diagnosis apparatus according to claim 2, wherein the processing circuitry defines the signals by using one selected from among a total sum of singular values, a largest singular value, and a high-rank singular value and defines the noise by using a singular value equal to or smaller than a threshold value.

6. The ultrasound diagnosis apparatus according to claim 2, wherein, when rank of the correlation matrix of the data sequence is not full rank, the processing circuitry estimates that the saturation is equal to or higher than a threshold value.

7. The ultrasound diagnosis apparatus according to claim 1, wherein
   the processing circuitry extracts moving member information from the data sequence,
   the processing circuitry generates image data based on the moving member information, and the processing circuitry causes the display to display the image data.

8. The ultrasound diagnosis apparatus according to claim 7, wherein the processing circuitry extracts the moving member information by performing a statistical calculation on a basis of the data sequence.

9. The ultrasound diagnosis apparatus according to claim 8, wherein the processing circuitry extracts moving member information with respect to each of sectional regions by performing the statistical calculation, on a basis of the sectional regions obtained by separating a scan range formed with a plurality of scanning lines into two or more regions.

10. The ultrasound diagnosis apparatus according to claim 7, wherein, when estimating that the saturation is equal to or higher than a threshold value, the processing circuitry corrects the moving member information.

11. The ultrasound diagnosis apparatus according to claim 10, wherein the processing circuitry extracts a power value as the moving member information and suppresses the extracted power value.

12. The ultrasound diagnosis apparatus according to claim 11, wherein
the processing circuitry generates correction information from the result of the estimation, and
the processing circuitry corrects the moving member information by using the correction information.

13. The ultrasound diagnosis apparatus according to claim 7, wherein, when estimating that the saturation is equal to or higher than a threshold value, the processing circuitry extracts the moving member information from the data sequence by raising a cut-off frequency of a filter used for extracting the moving member information from the data sequence so as to be higher than a cut-off frequency used when the saturation is lower than the threshold value.

14. A medical image processing apparatus comprising processing circuitry configured:
to generate a piece of reflected-wave data by performing a phased addition process while using reflected-wave signals generated by transmitting an ultrasound wave with respect to a same scanning line and to estimate saturation of the reflected-wave signals observed before the phased addition process on a basis of a relationship between signals and noise in a data sequence represented by a set made up of pieces of the reflected-wave data;
to output a result of the estimation; and
to cause a display to display data based on the result of the estimation.

15. A medical image processing method implemented by a computer, comprising:
generating a piece of reflected-wave data by performing a phased addition process while using reflected-wave signals generated by transmitting an ultrasound wave with respect to a same scanning line;
estimating saturation of the reflected-wave signals observed before the phased addition process on a basis of a relationship between signals and noise in a data sequence represented by a set made up of pieces of the reflected-wave data;
outputting a result of the estimation; and
causing a display to display data based on the result of the estimation.

* * * * *